US010448885B2

(12) United States Patent
Schmid

(10) Patent No.: US 10,448,885 B2
(45) Date of Patent: Oct. 22, 2019

(54) CONFIRMATION OF DELIVERY OF MEDICATION TO A HOST

(71) Applicant: Insulet Corporation, Billerica, MA (US)

(72) Inventor: Kevin G. Schmid, Boxford, MA (US)

(73) Assignee: Insulet Corporation, Acton, MA (US)

( * ) Notice: Subject to any disclaimer, the term of this patent is extended or adjusted under 35 U.S.C. 154(b) by 250 days.

(21) Appl. No.: 15/180,724

(22) Filed: Jun. 13, 2016

(65) Prior Publication Data

US 2016/0361013 A1 Dec. 15, 2016

Related U.S. Application Data

(60) Provisional application No. 62/174,641, filed on Jun. 12, 2015.

(51) Int. Cl.
*A61B 5/00* (2006.01)
*A61M 5/158* (2006.01)
(Continued)

(52) U.S. Cl.
CPC .......... *A61B 5/4848* (2013.01); *A61B 5/0022* (2013.01); *A61B 5/14532* (2013.01);
(Continued)

(58) Field of Classification Search
CPC .......... A61B 2562/0295; A61B 5/0022; A61B 5/14532; A61B 5/4839; A61B 5/4848;
(Continued)

(56) References Cited

U.S. PATENT DOCUMENTS 5,586,553 A * 12/1996 Halili ................ A61B 5/14532
600/316
7,018,360 B2 3/2006 Flaherty et al.
(Continued)

FOREIGN PATENT DOCUMENTS

WO 2014136105 A1 9/2014

OTHER PUBLICATIONS

Preliminary Report on Patentability dated Dec. 21, 2017, issued in PCT International Patent Application No. PCT/US2016/037189, 12 pages.
(Continued)

*Primary Examiner* — Quynh-Nhu H. Vu
(74) *Attorney, Agent, or Firm* — Grossman Tucker Perreault & Pfleger, PLLC

(57) ABSTRACT

A method of treating a host with a medication, comprising assigning a unique identifier to a host treatment apparatus; assigning a unique identifier to the host; storing the unique host identifier and the unique host treatment apparatus identifier on at least one remote server of a network and associating the unique host identifier and the unique host treatment apparatus identifier on the at least one remote server such that the unique host identifier and the unique host treatment apparatus identifier are exclusively associated to each other; activating the host treatment apparatus; coupling the host medication delivery device to the host; operating the host medication delivery device to deliver the medication contained in the host medication delivery device to the host; and operating the host treatment apparatus such that the host treatment apparatus communicates wirelessly to the at least one remote server an operational status of the host medication delivery device.

15 Claims, 23 Drawing Sheets

(51) Int. Cl.
*G06F 19/00* (2018.01)
*A61B 5/145* (2006.01)
*A61M 5/172* (2006.01)
*A61M 5/142* (2006.01)

(52) U.S. Cl.
CPC .......... *A61B 5/4839* (2013.01); *A61M 5/158* (2013.01); *A61M 5/1723* (2013.01); *G06F 19/3456* (2013.01); *A61B 2562/0295* (2013.01); *A61M 2005/14252* (2013.01); *A61M 2205/3584* (2013.01); *A61M 2205/702* (2013.01); *A61M 2230/201* (2013.01)

(58) Field of Classification Search
CPC .......... A61M 2005/14252; A61M 2205/3584; A61M 2205/702; A61M 2230/201; A61M 5/158; A61M 5/1723; G06F 19/00; G06F 19/3456
See application file for complete search history.

(56) References Cited

U.S. PATENT DOCUMENTS

| | | |
|---|---|---|
| 7,128,727 B2 | 10/2006 | Flaherty et al. |
| 7,144,384 B2 | 12/2006 | Gorman et al. |
| 2004/0010507 A1 | 1/2004 | Bellew |
| 2005/0238507 A1 | 10/2005 | Diianni et al. |
| 2006/0282290 A1 | 12/2006 | Flaherty et al. |
| 2007/0118405 A1 | 5/2007 | Campbell et al. |
| 2009/0062767 A1* | 3/2009 | Van Antwerp ....... A61B 5/6846 604/504 |
| 2009/0112769 A1* | 4/2009 | Dicks ..................... G06Q 50/22 705/51 |
| 2011/0047499 A1* | 2/2011 | Mandro ................. A61M 5/142 715/780 |
| 2011/0118694 A1* | 5/2011 | Yodfat ................... G06F 19/00 604/500 |
| 2011/0124996 A1* | 5/2011 | Reinke ............. A61M 5/14248 600/365 |
| 2012/0029941 A1* | 2/2012 | Malave ................. A61M 5/172 705/3 |
| 2014/0180203 A1* | 6/2014 | Budiman ........... A61B 5/14532 604/66 |
| 2015/0038898 A1 | 2/2015 | Palmer et al. |

OTHER PUBLICATIONS

PCT Search Report and Written Opinion dated Sep. 9, 2016, received in corresponding PCT Application No. PCT/US16/37189, 14 pgs.

* cited by examiner

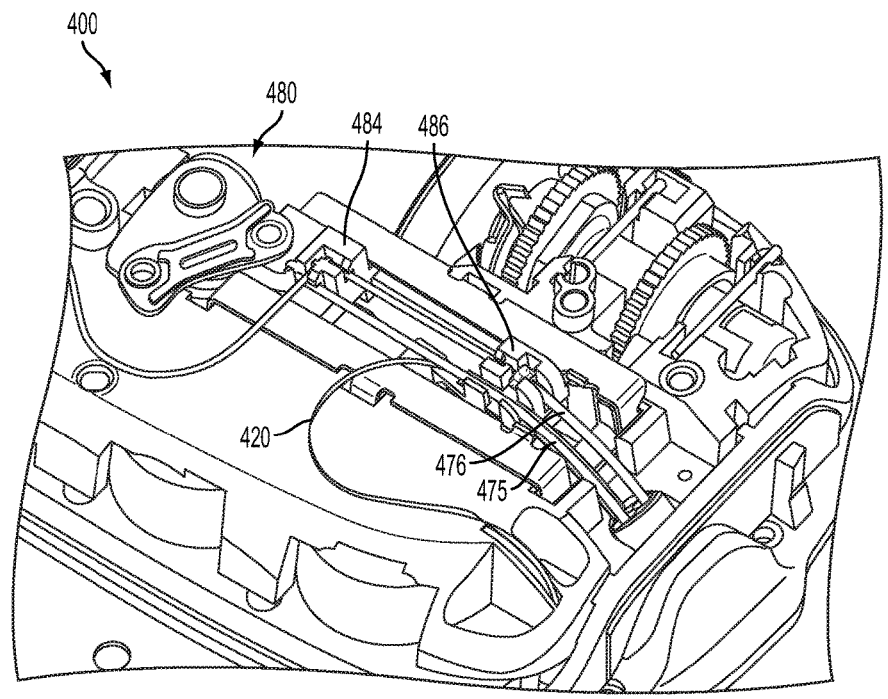
FIG. 39
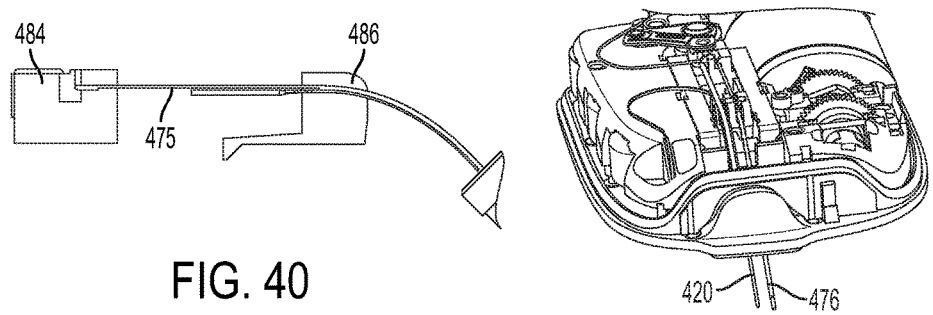
FIG. 40
FIG. 41

CONFIRMATION OF DELIVERY OF MEDICATION TO A HOST

CROSS-REFERENCE TO RELATED APPLICATIONS

This application claims the benefit of U.S. provisional application Ser. No. 62/174,641 filed Jun. 12, 2015, which is incorporated by reference in its entirety.

TECHNICAL FIELD

The present disclosure relates to methods of delivering medication to a host with a medication delivery device, and more particularly, methods of monitoring the medication delivery device, as well as one or more physiological parameters associated with tissue of the host, to confirm subcutaneous delivery of medication.

BACKGROUND INFORMATION

In a patient with diabetes mellitus, ambulatory infusion pumps have been used to deliver insulin to the patient. These ambulatory infusion pumps have the ability to offer insulin delivery profiles including variable basal rates and bolus requirements. The ability to carefully control insulin delivery can result in better efficacy of the medication and therapy, and less toxicity to the patient.

Some existing ambulatory infusion pumps include a reservoir to contain insulin and use electromechanical pumping or metering technology to deliver the insulin via tubing to a needle and/or soft cannula that is inserted subcutaneously into the patient. These existing devices allow control and programming via electromechanical buttons or switches located on the housing of the device. The devices include visual feedback via text or graphic screens and may include alert or warning lights and audio or vibration signals and alarms. Such devices are typically worn in a harness or pocket or strapped to the body of the patient.

Some infusion pumps have been designed to be relatively small, low cost, light-weight, and easy-to-use. One example of such a pump is the OMNIPOD® insulin infusion pump available from Insulet Corporation. Examples of infusion pumps are also described in greater detail, for example, in U.S. Pat. Nos. 7,128,727; 7,018,360; and 7,144,384 and U.S. Patent Application Publication Nos. 2007/0118405, 2006/0282290, 2005/0238507, and 2004/0010507, which are fully incorporated herein by reference. These pumps include insertion mechanisms for causing a transcutaneous access tool, such as a needle and/or soft cannula, to be inserted into a patient. Although such pumps are effective and provide significant advantages over other insulin infusion pumps, there is a need for continued improvement.

Complications arising from diabetes mellitus may be reduced by careful management that includes regular checking of glucose concentration levels, typically at numerous times of the day depending on the specific type of diabetes mellitus, with Type 1 patients generally having to check glucose levels more often than Type 2 patients.

Most diabetes patients rely on glucose strips along with hand-held glucose meters that record glucose levels in blood drawn via finger pricking, which may be referred to as user-dependent (self-monitoring) of blood glucose. However, the pain associated with finger pricking, together with the inability of test strips to reflect whether the glucose level of a patient is increasing or decreasing at any point in time with user-dependent (self-monitoring) of blood glucose level is problematic.

Continuous glucose monitoring incorporated into an ambulatory infusion pump may be beneficial to patients by eliminating many of the problems associated with self monitoring, as well as help identify glucose trends to physicians who may then better optimize treatment plans.

In addition, confirmation of medication delivery by a medication delivery device such as an ambulatory infusion pump is desirable to ensure proper treatment. As such, it would be beneficial for such devices to confirm proper operation and actual delivery of the medication.

SUMMARY

The present disclosure provides devices and methods of treating a host, such as a patient, with a medication. Moreover, the present disclosure provides devices and methods of delivering medication to a host with a medication delivery device, and more particularly, methods of monitoring the medication delivery device, as well as one or more physiological parameters associated with tissue of the host, to confirm subcutaneous delivery of medication.

In at least one embodiment, a method of treating a host with a medication may comprise assigning a unique identifier to a host treatment apparatus comprising a host medication delivery device which delivers medication into tissue of the host, wherein the unique host treatment apparatus identifier distinguishes the host treatment apparatus from a plurality of other host treatment apparatuses each having a unique host treatment apparatus identifier; assigning a unique identifier to the host to be treated by the host treatment apparatus wherein the unique host identifier distinguishes the host from a plurality of other hosts each having a unique host identifier; storing the unique host identifier and the unique host treatment apparatus identifier on at least one remote server of a network, and associating the unique host identifier and the unique host treatment apparatus identifier on the at least one remote server of the network such that the unique host treatment apparatus identifier is exclusively associated with the unique host identifier; filling the host medication delivery device with medication; activating the host treatment apparatus; coupling the host medication delivery device to the host such that the host medication delivery device is arranged to deliver the medication contained in the host medication delivery device to the host; operating the host medication delivery device to deliver the medication contained in the host medication delivery device to the host; and operating the host treatment apparatus such that the host treatment apparatus communicates wirelessly to the at least one remote server of the network an operational status of the host medication delivery device.

In at least one embodiment, the step(s) of storing the unique host identifier and the unique host treatment apparatus identifier on at least one remote server of a network, and associating the unique host identifier and the unique host treatment apparatus identifier on the at least one remote server of the network such that the unique host treatment apparatus identifier is exclusively associated to the unique host identifier may further comprise associating the unique host identifier and the unique host treatment apparatus identifier in a computer software program which resides on the at least one remote server of the network; and the step of operating the host treatment apparatus such that the host treatment apparatus communicates wirelessly to at least one remote server of the network an operational status of the host medication delivery device may further comprise operating the host treatment apparatus such that the host treatment apparatus communicates wirelessly to the computer software program residing on the at least one remote server of the network an operational status of the host medication delivery device.

In at least one embodiment, the step of operating the host treatment apparatus such that the host treatment apparatus communicates wirelessly to the at least one remote server of the network an operational status of the host medication delivery device may further comprise operating the host treatment apparatus such that the host treatment apparatus communicates wirelessly to the at least one remote server of the network an operational status of medication delivery from the host medication delivery device to the host.

In at least one embodiment, the step of operating the host treatment apparatus such that the host treatment apparatus communicates wirelessly to the at least one remote server of the network an operational status of medication delivery from the host medication delivery device to the host may further comprise operating the host treatment apparatus such that the host treatment apparatus communicates wirelessly to the at least one remote server of the network a successful status or an unsuccessful status of medication delivery from the host medication delivery device to the host.

In at least one embodiment, the at least one remote server of the network receives a wireless communication from the host treatment apparatus as to the operational status of the host medication delivery device; and in response to the wireless communication from the host treatment apparatus as to the operational status of the host medication delivery device, the at least one remote server of the network reports the operational status of the host medication delivery device to at least one client user of the network.

In at least one embodiment, the unique identifier of the host treatment apparatus uniquely identifies the host medication delivery device.

In at least one embodiment, the unique identifier of the host treatment apparatus is a unique identifier of the host medication delivery device.

In at least one embodiment, the host treatment apparatus further comprises a host remote control device, wherein the host medication delivery device and the host remote control device are configured to communicate wirelessly to each other.

In at least one embodiment, the host medication delivery device includes a sensor, wherein the sensor is used to measure a physiological parameter associated with the tissue; and the method of treating a host with a medication further comprises introducing the host medication delivery device including the sensor into the tissue; delivering the medication into the tissue of the host; and confirming delivery of the medication from the host medication delivery device to the host, wherein confirming delivery of the medication comprises using the sensor to measure the physiological parameter within a predetermined time period after delivery of the medication.

In at least one embodiment, the method further comprises introducing the host medication delivery device including the sensor into the tissue such that the tissue is in contact with the sensor; and forming a depot in the tissue with the medication, wherein the depot reduces the tissue contact with the sensor.

In at least one embodiment, the predetermined time period is less than a time required for the depot to be completely absorbed into the tissue and the tissue reestablishes contact with the sensor where the depot was located.

In at least one embodiment, confirming delivery of the medication from the host medication delivery device to the host further comprises determining a value of the physiological parameter measured within the predetermined time period after delivery of the medication; providing a predetermined representative value for the physiological parameter, wherein the predetermined representative value of the physiological parameter is stored with at least one of the host treatment apparatus and the at least one remote server of the network; and determining that the measured value of the physiological parameter within the predetermined time period after delivery of the medication is less than, or greater than, the predetermined representative value for the physiological parameter stored with at least one of the host treatment apparatus and the at least one remote server of the network.

In at least one embodiment, after introducing the host medication delivery device including the sensor into the tissue, the method further comprises using the sensor to measure the physiological parameter before delivering the medication into the tissue; and wherein confirming delivery of the medication from the host medication delivery device to the host further comprises determining a value of the physiological parameter measured before delivering the medication; determining a value of the physiological parameter measured within the predetermined time period after delivery of the medication; and determining that the value of the physiological parameter measured within the predetermined time after delivery of the medication is less than, or greater than, the value of the physiological parameter measured before delivering the medication into the tissue.

In at least one embodiment, after introducing the host medication delivery device including the sensor into the tissue, the method further comprises using the sensor to measure the physiological parameter before delivering the medication into the tissue; and wherein confirming delivery of the medication from the host medication delivery device to the host further comprises determining a value of the physiological parameter measured before delivering the medication; determining a value of the physiological parameter measured within the predetermined time period after delivery of the medication; determining a numerical difference between the value of the physiological parameter measured before delivering the medication into the tissue, and the value of the physiological parameter measured within the predetermined time after delivering the medication into the tissue; providing a predetermined representative value for the numerical difference of the physiological parameter, wherein the predetermined representative value for the numerical difference of the physiological parameter is stored with at least one of the host treatment apparatus and the at least one remote server of the network; and determining the numerical difference between the two measured values of the physiological parameter is greater than the predetermined representative value for the numerical difference of the physiological parameter stored with at least one of the host treatment apparatus and the at least one remote server of the network.

In at least one embodiment, after introducing the host medication delivery device including the sensor into the tissue, the method further comprises using the sensor to measure the physiological parameter before delivering the medication into the tissue; and wherein confirming delivery of the medication from the host medication delivery device to the host further comprises determining a value of the physiological parameter measured before delivering the medication; determining a value of the physiological parameter measured within the predetermined time period after delivery of the medication; determining a percentage change between the value of the physiological parameter measured before delivering the medication into the tissue, and the value of the physiological parameter measured within the predetermined time after delivering the medication into the tissue; providing a predetermined representative value for the percentage change of the physiological parameter, wherein the predetermined representative value for the percentage change of the physiological parameter is stored with at least one of the host treatment apparatus and the at least one remote server of the network; and determining the percentage change between the two measured values of the physiological parameter is greater than the predetermined representative value for the percentage change of the physiological parameter stored with at least one of the host treatment apparatus and the at least one remote server of the network.

In at least one embodiment, the host medication delivery device includes a sensor, wherein the sensor is used to measure a physiological parameter associated with the tissue; and the method further comprises introducing the host medication delivery device including the sensor into the tissue such that the tissue is in contact with the sensor; delivering the medication into the tissue of the host; forming a depot in the tissue with the medication, wherein the sensor is at least partially within the depot and the depot reduces the tissue contact with the sensor; and confirming delivery of the medication from the host medication delivery device to the host, wherein confirming delivery of the medication comprises using the sensor to measure the physiological parameter while the sensor is within the depot.

In at least one embodiment, confirming delivery of the medication from the host medication delivery device to the host further comprises determining a value of the physiological parameter while the sensor is within the depot; providing a predetermined representative value for the physiological parameter, wherein the predetermined representative value of the physiological parameter is stored with at least one of the host treatment apparatus and the at least one remote server of the network; and determining that the measured value of the physiological parameter while the sensor is within the depot is less than, or greater than, the predetermined representative value for the physiological parameter stored with at least one of the host treatment apparatus and the at least one remote server of the network.

In at least one embodiment, after introducing the host medication delivery device including the sensor into the tissue, the method further comprises using the sensor to measure the physiological parameter before delivering the medication into the tissue; and wherein confirming delivery of the medication from the host medication delivery device to the host further comprises determining a value of the physiological parameter measured before delivering the medication; determining a value of the physiological parameter measured while the sensor is within the depot; and determining that the value of the physiological parameter measured while the sensor is within the depot is less than, or greater than, the value of the physiological parameter measured before delivering the medication into the tissue.

In at least one embodiment, after introducing the host medication delivery device including the sensor into the tissue, the method further comprises using the sensor to measure the physiological parameter before delivering the medication into the tissue; and wherein confirming delivery of the medication from the host medication delivery device to the host further comprises determining a value of the physiological parameter measured before delivering the medication; determining a value of the physiological parameter measured while the sensor is within the depot; determining a numerical difference between the value of the physiological parameter measured before delivering the medication into the tissue, and the value of the physiological parameter measured while the sensor is within the depot; providing a predetermined representative value for the numerical difference of the physiological parameter, wherein the predetermined representative value for the numerical difference of the physiological parameter is stored with at least one of the host treatment apparatus and the at least one remote server of the network; and determining the numerical difference between the two measured values of the physiological parameter is greater than a predetermined representative value for the numerical difference of the physiological parameter stored with at least one of the host treatment apparatus and the at least one remote server of the network.

In at least one embodiment, after introducing the host medication delivery device including the sensor into the tissue, the method further comprises using the sensor to measure the physiological parameter before delivering the medication into the tissue; and wherein confirming delivery of the medication from the host medication delivery device to the host further comprises determining a value of the physiological parameter measured before delivering the medication; determining a value of the physiological parameter measured while the sensor is within the depot; determining a percentage change between the value of the physiological parameter measured before delivering the medication into the tissue, and the value of the physiological parameter measured while the sensor is within the depot; providing a predetermined representative value for the percentage change of the physiological parameter, wherein the predetermined representative value for the percentage change of the physiological parameter is stored with at least one of the host treatment apparatus and the at least one remote server of the network; and determining the percentage change between the two measured values of the physiological parameter is greater than a predetermined representative value for the percentage change of the physiological parameter stored with at least one of the host treatment apparatus and the at least one remote server of the network.

BRIEF DESCRIPTION OF THE DRAWINGS

These and other features and advantages will be better understood by reading the following detailed description, taken together with the drawings wherein:

FIGS. 35-41 are views of another embodiment of a fluid delivery device including an oval trocar for inserting a monitor test strip transcutaneously;

DETAILED DESCRIPTION

Figure 1:
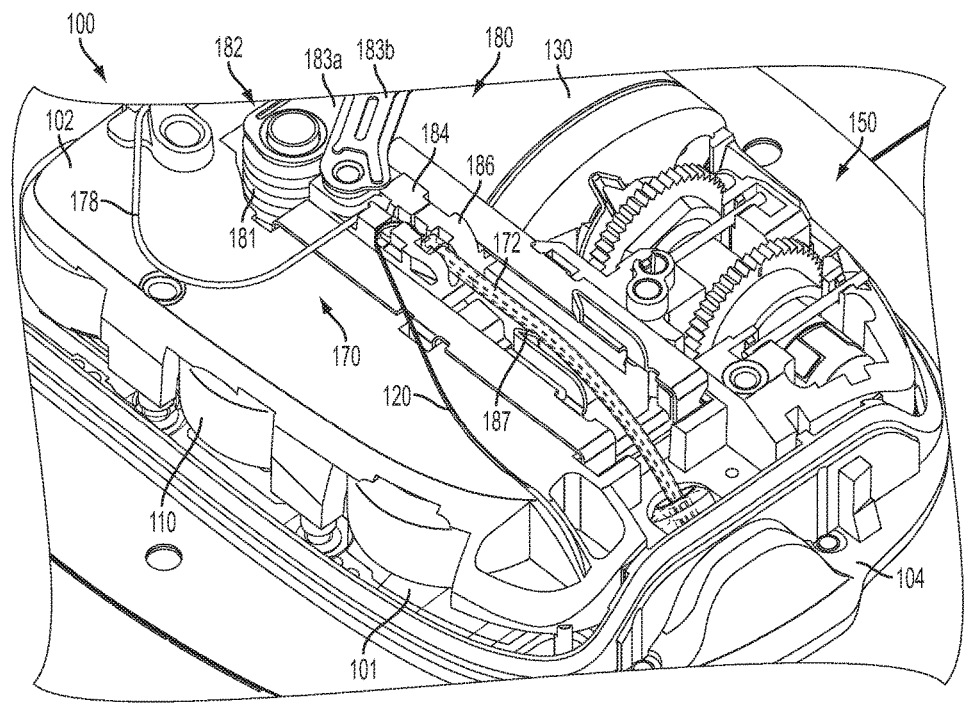
FIG. 1 is a top perspective view of a fluid delivery device with a transcutaneous access tool insertion mechanism in a pre-deployment position, consistent with the present disclosure.
Figure 2:
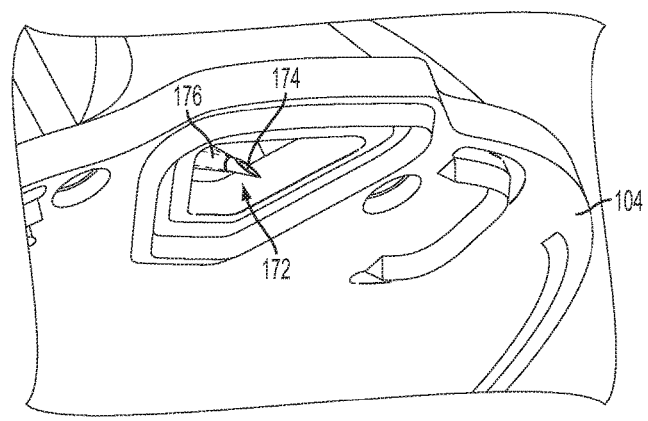
FIG. 2 is a bottom perspective view of a needle and cannula retracted into the fluid delivery device in the pre-deployment position shown in FIG. 1.
Figure 3:
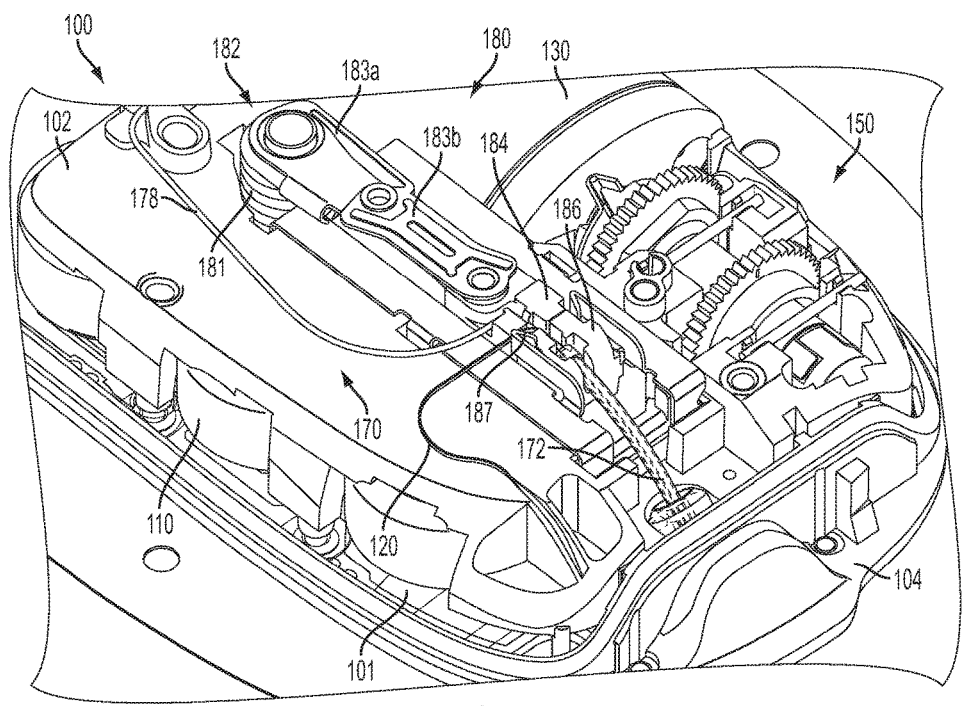
FIG. 3 is a top perspective view of the fluid delivery device shown in FIG. 1 with the insertion mechanism in an intermediate position.
Figure 4:
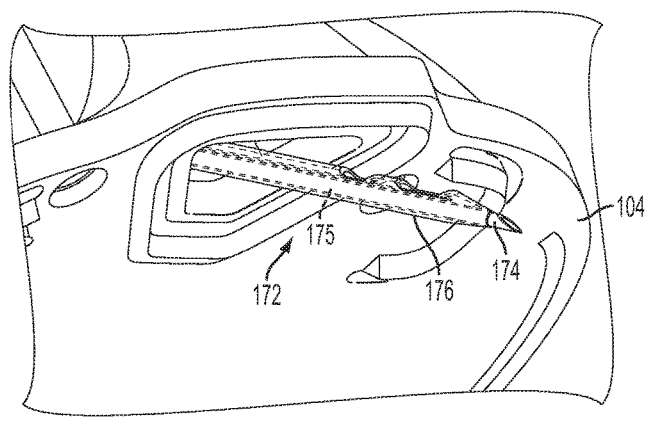
FIG. 4 is a bottom perspective view of the needle and cannula extending from the fluid delivery device in the intermediate position shown in FIG. 3.

Operation of a medical device, comprising a host treatment apparatus, may be monitored as part of a computer network to confirm proper operation of the host treatment apparatus, as well as delivery of medication from the host treatment apparatus to a host. In addition, a physiological parameter associated with tissue of a host may be monitored in tissue subcutaneously to confirm subcutaneous delivery of medication to the host. More particularly, such may involve delivering medication subcutaneously to the host with a medical device which includes a sensor used to measure the physiological parameter, particularly within a predetermined time period after delivery of the medication. Such may also or otherwise involve forming a depot in the tissue with the medication, and using the sensor to measure the physiological parameter while the sensor is at least partially within the depot.

Methods for monitoring consistent with the present disclosure may be performed using a medication delivery device as disclosed herein to deliver the medication to the host subcutaneously. The medication delivery device may more particularly be referred to herein as a fluid delivery device, particularly as the medication disclosed herein is in liquid form.

The fluid delivery device may particularly deliver a therapeutic fluid to the host via a transcutaneous access tool, such as a needle/trocar and/or a cannula. A transcutaneous access tool insertion mechanism may be used to deploy the transcutaneous access tool, for example, by inserting and retracting a needle/trocar in a single, uninterrupted motion. The insertion mechanism may also provide an increasing insertion force as the needle/trocar moves in the insertion direction. The fluid delivery device may also include a clutch mechanism to facilitate filling a reservoir and engagement of a drive mechanism for driving fluid out of the reservoir. In certain embodiments, the fluid delivery device may comprise an ambulatory insulin infusion device.

In other embodiments, a fluid delivery device may be used to deliver a therapeutic fluid to a host with integrated monitoring, such as continuous glucose monitoring (CGM). In these embodiments, the fluid deliver device may include a transcutaneous access tool configured to introduce a monitoring test strip through the skin of the host, for example, using one or more needles, cannulas and/or trocars.

Referring to FIGS. 1-6, one embodiment of a fluid (medication) delivery device 100a is shown and described. In the exemplary embodiment, the fluid (medication) delivery device 100a is used to subcutaneously deliver a fluid, such as a liquid medicine (e.g. insulin), to a person or an animal, which may be referred to as a host. Those skilled in the art will recognize that the host fluid (medication) delivery device 100a may be used to deliver other types of fluids, such as saline. The host fluid (medication) delivery device 100a may be used to deliver fluids in a controlled manner, for example, according to fluid delivery profiles accomplishing basal and bolus requirements, continuous infusion and variable flow rate delivery.

As such, the fluid may by a liquid dosage form including one or more active pharmaceutical ingredients which may include analgesic drugs; anesthetic drugs; anti-arthritic drugs; anti-bacterial drugs; anti-biotic drugs; anti-cholesterol drugs; anti-coagulant drugs; anti-cancer drugs; anti-convulsant drugs; anti-depressant drugs; anti-diabetic drugs; anti-gastrointestinal reflux drugs; anti-hypertension drugs; anti-infection drugs; anti-inflammatory drugs; anti-migraine drugs; anti-muscarinic drugs; anti-neoplastic drugs; anti-obesity; anti-parasitic drugs; anti-protozoal drugs; anti-psychotic drugs; anti-stroke; anti-ulcer drugs; anti-viral drugs; cardiovascular drugs; central nervous system drugs; digestive tract drugs; diuretic drugs; fertility drugs; gastrointestinal tract drugs; genitourinary tract drugs; hormonal drugs; immunologic agents; metabolic drugs; psychotherapeutic drugs; pulmonary drugs; radiological drugs; respiratory drugs; and sedative drugs. The one or more active pharmaceutical ingredients may also include biologics.

According to one embodiment, the host fluid (medication) delivery device 100a may include one or more batteries 110 for providing a power source, a fluid reservoir 130 for holding a fluid, a fluid drive mechanism 150 for driving the fluid out of the reservoir 130, a fluid passage mechanism 170 for receiving the fluid from the reservoir 130 and passing the fluid to a destination via a transcutaneous access tool 172, and a transcutaneous access tool insertion mechanism 180 for deploying the transcutaneous access tool 172. The host fluid (medication) delivery device 100a may include a circuit board 101 including a microcontroller (processor), with control circuitry and a communication element for remotely controlling the device and a chassis 102 that provides mechanical and/or electrical connections between components of the host fluid (medication) delivery device 100a. The host fluid (medication) delivery device 100a may also include a housing 104 to enclose the circuit board 101, the chassis 102, and the components 110, 130, 150, 170, 180.

The host fluid (medication) delivery device 100a may also include integrated monitoring such as continuous glucose monitoring (CGM). A monitor test strip 120, coupled to a monitor (not shown), of the host fluid (medication) delivery device 100a may be introduced by the transcutaneous access tool 172 subcutaneously. One example of the monitor test strip is a CGM test strip which may be understood as a glucose sensor configured to test for a concentration level of glucose in the interstitial fluid (ISF) and/or blood of a host. The host fluid (medication) delivery device 100a may be configured to receive data from the monitoring test strip concerning a glucose concentration level of the host, and determining an output of insulin from the reservoir based on the glucose concentration level.

The transcutaneous access tool 172 includes an introducer trocar or needle 174 at least partially positioned within a lumen 175 of a cannula 176 (e.g., a soft flexible cannula), which is capable of passing the fluid into the host. In particular, the introducer needle/trocar 174 may initially penetrate the skin such that both the introducer needle/trocar 174 and the cannula 176 are introduced (inserted) into the host, and the introducer needle/trocar 174 may then be retracted within the cannula 176 such that the cannula 176 remains inserted. A fluid path, such as tubing 178, fluidly couples the reservoir 130 to the lumen 175 of cannula 176 of the transcutaneous access tool 172. The transcutaneous access tool 172 may also be used to introduce a monitoring test strip subcutaneously into the host for monitoring purposes, as described in greater detail below.

Figure 5:
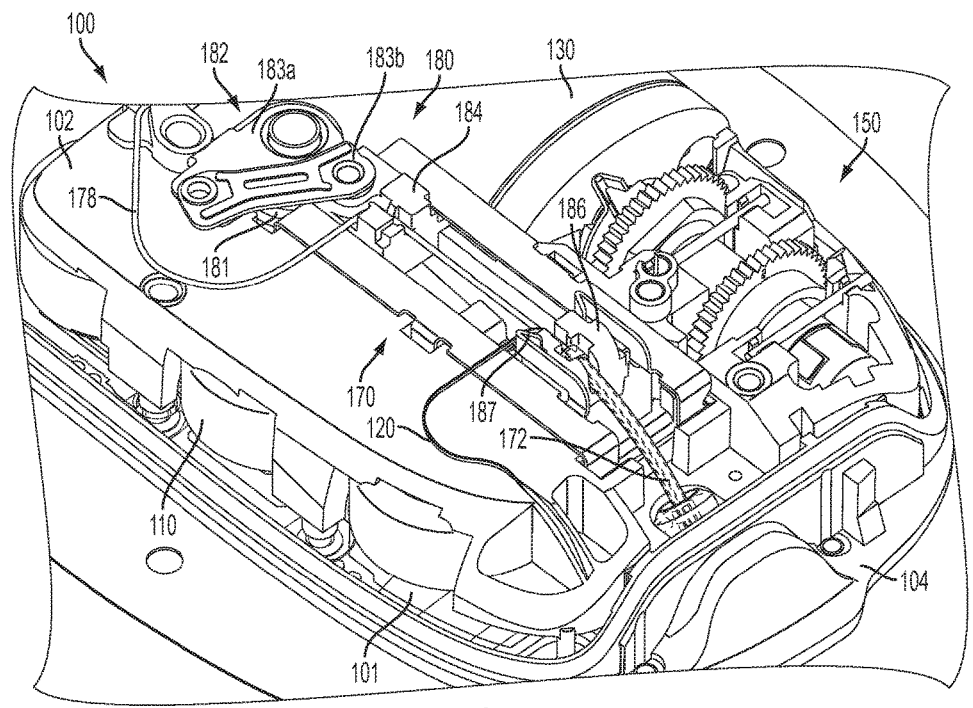
FIG. 5 is a top perspective view of the fluid delivery device shown in FIG. 1 with the insertion mechanism in a post-deployment position.
Figure 6:
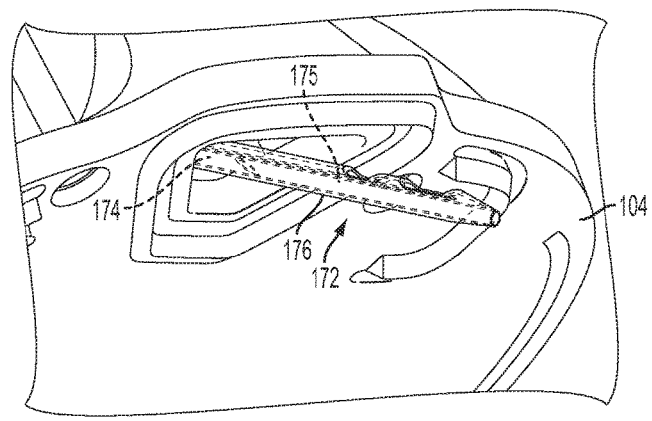
FIG. 6 is a bottom perspective view of the cannula extending from the fluid delivery device in the post-deployment position shown in FIG. 5.

The transcutaneous access tool insertion mechanism 180 is coupled to the transcutaneous access tool 172 to deploy the transcutaneous access tool 172, for example, by inserting the needle/trocar 174 and cannula 176 through the skin of a host and retracting the needle/trocar 174. In the illustrated embodiment, the insertion mechanism 180 includes a spring-biased linkage mechanism 182 and sliding members 184, 186 coupled to the needle/trocar 174 and cannula 176, respectively, for moving the needle/trocar 174 and cannula 176 in the insertion direction and for moving the needle/trocar 174 in the retraction direction. In a single, uninterrupted motion, the spring-biased linkage mechanism 182 moves from a pre-deployment position (FIG. 1) with both needle/trocar 174 and cannula 176 retracted (FIG. 2) to an intermediate position (FIG. 3) with both needle/trocar 174 and cannula 176 inserted (FIG. 4) to a post-deployment position (FIG. 5) with the needle/trocar 174 retracted and the cannula 176 inserted (FIG. 6).

One embodiment of the spring-biased linkage mechanism 182 includes a helical torsion spring 181 and first and second linkages 183a, 183b coupled between the torsion spring 181 and the first sliding member 184. Energy stored in the torsion spring 181 applies a force to the linkages 183a, 183b, which applies a force to the first sliding member 184 to move the first sliding member 184 in both the insertion direction and in the retraction direction. In the pre-deployment position (FIG. 1), the torsion spring 181 is loaded and the sliding members 184, 186 are locked and prevented from moving. When the sliding members 184, 186 are released, the energy stored in the torsion spring 181 causes the first linkage 183a to rotate (e.g., clockwise as shown), which applies a force to the first sliding member 184 through the second linkage 183b causing the first sliding member 184 with the needle/trocar 174 to move (with the second sliding member 186) in the insertion direction. In the intermediate position (FIG. 3), the linkages 183a, 183b are fully extended with the needle/trocar 174 and cannula 176 being inserted, the second sliding member 186 is locked, and the remaining energy stored in the torsion spring 181 causes the first linkage 183a to continue to rotate, which applies an opposite force to the first sliding member 184 through the second linkage 183b causing the first sliding member 184 with the needle/trocar 174 to move in the retraction direction to the post-deployment position (FIG. 5). In the illustrated embodiment, the second sliding member 186 is locked against retraction by one or more latches 187. Thus, in the foregoing manner, the continuous uninterrupted clockwise rotation of first linkage 183a via the energy of torsion spring 181 provides the transcutaneous access tool insertion mechanism 180 with the ability to insert and retract the needle/trocar 174 in a single, uninterrupted motion.

The spring-biased linkage mechanism 182 allows a single spring and motion to achieve both the insertion and retraction and has a relatively small size. The spring-biased linkage mechanism 182 also reduces the static stresses caused by locking and holding back the sliding members 184, 186 and provides a smoother and more comfortable needle/trocar insertion because of the way the linkages 183a, 183b vector the forces applied to the sliding members 184, 186. The static forces on the sliding members 184, 186 are relatively small in the pre-deployment position when the linkages 183a, 183b are fully retracted. When the deployment starts and the linkages 183a, 183b start to become extended, the insertion forces increase because the force vectors increase in the insertion direction as the linkages extend 183a, 183b until a maximum insertion force is reached at the fully extended, intermediate position. By gradually increasing the insertion forces, the needle/trocar insertion and retraction is smoother, quieter and less painful.

Figure 7:
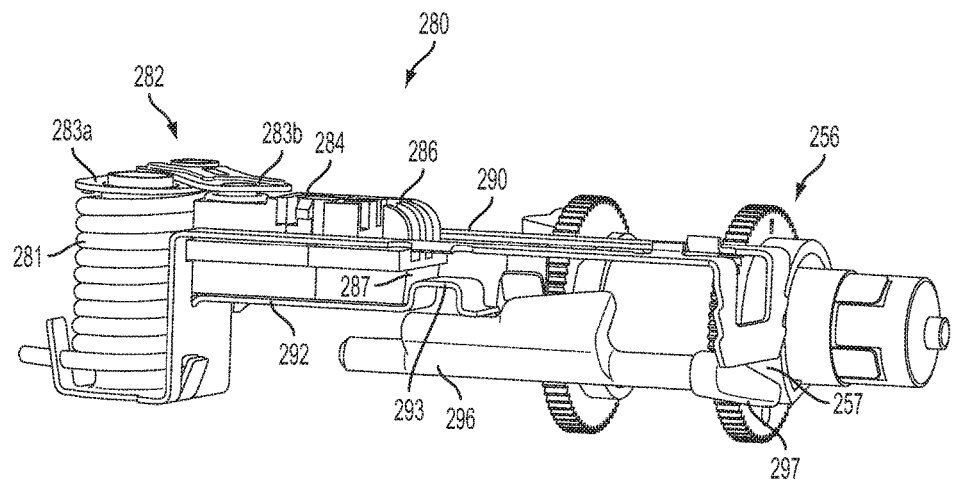
FIG. 7 is a side perspective view of another embodiment of the insertion mechanism, consistent with the present disclosure, in a pre-deployment position.
Figure 8:
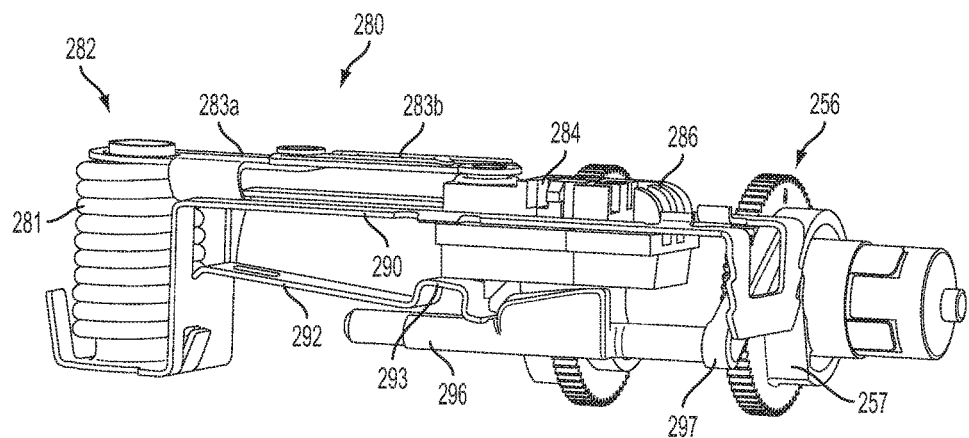
FIG. 8 is a side perspective view of the insertion mechanism shown in FIG. 7 in an intermediate position.

Another embodiment of an insertion mechanism 280 is shown in greater detail in FIGS. 7-10. The sliding members 284, 286 are slidably received in a frame 290 and moved by a spring-biased linkage mechanism 282 including torsion spring 281 and linkages 283a, 283b. In this embodiment, a cam finger 292 (e.g., extending from the frame 290) engages beneath one or both of the sliding members 284, 286 to lock the sliding members in the retracted or pre-deployment position (FIG. 7). In this pre-deployment position, the cam finger 292 is held against the sliding members 284, 286 by a release bar 296, which may be moved (rotated) to allow the cam finger 292 to move and release the sliding members 284, 286 (FIG. 8). The cam finger 292 may be biased in a downward direction and/or the second sliding member 286 may include a cam surface 287 to help facilitate movement along the cam finger 292 over locking mechanism 293 upon actuation.

The release bar 296 includes a lever 297 for pivoting the release bar 296 between an engaged position against the cam finger 292 (FIG. 7) and a disengaged position releasing the cam finger 292 (FIG. 8). The release bar 296 may be biased toward the disengaged position and held against the cam finger 292 in the engaged position until the lever 297 is released allowing the release bar 296 to move to the disengaged position. In the illustrated embodiment, the lever 297 engages a rotating surface 257 of a drive wheel 256 of the fluid drive mechanism 150 such that the lever 297 is held in the engaged position for part of the rotation and is released at a certain point during the rotation (e.g., when a flat portion of the rotating surface 257 allows the lever 297 to move).

Figure 9:
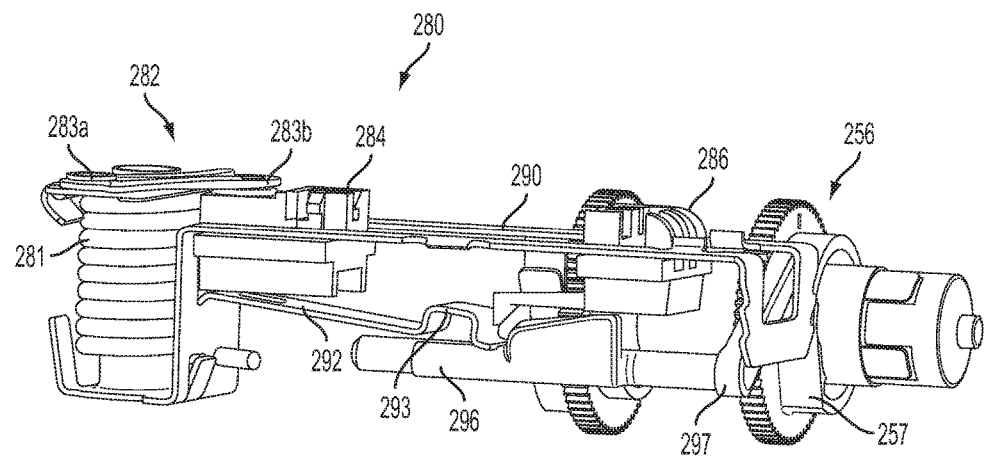
FIG. 9 is a side perspective view of the insertion mechanism shown in FIG. 7 in a post-deployment position.
Figure 10:
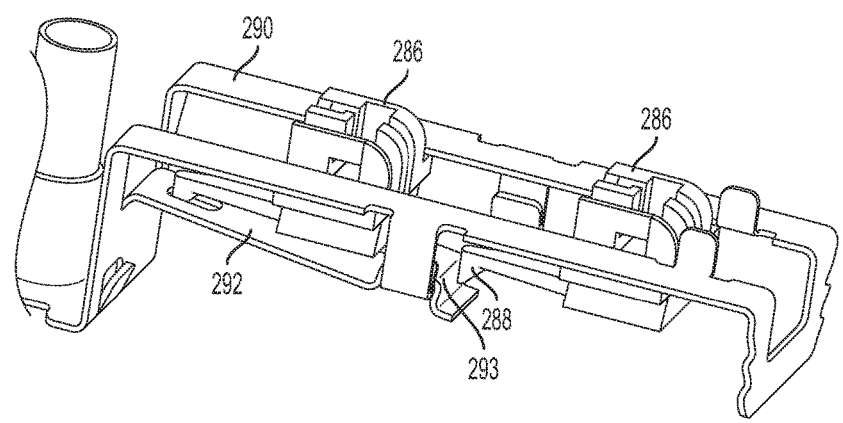
FIG. 10 is a top perspective view of the second sliding member of the insertion mechanism shown in FIG. 7 locked in the pre-deployment and post-deployment positions.

As shown in FIGS. 9 and 10, the cam finger 292 may also be used to lock the second sliding member 286 in the insertion position. A locking portion 288 of the second sliding member 286 engages a locking portion 293 of the cam finger 292 when the linkage mechanism 282 is fully extended in the intermediate position and prevents the second sliding member 286 from retracting such that the cannula remains inserted. As discussed above, the second sliding member 286 may also be locked by one or more latches (not shown) extending from a top of the frame 290.

Referring to FIGS. 11-16, one embodiment of the fluid drive mechanism 150 uses a clutch mechanism 160 to facilitate filling of the reservoir 130 and engagement of the fluid drive mechanism 150 for driving fluid out of the reservoir 130. The fluid drive mechanism 150 includes a first threaded member in the form of an elongated shaft such as a threaded drive rod or leadscrew 152, with external threads extending from a plunger 136 received in the reservoir 130 and sealed with an o-ring 137 against the inside surface of the reservoir 130. The leadscrew 152 and plunger 136 may be an inseparable, insert-molded assembly. A second threaded member in the form of an elongated shaft such as a tube nut 154 with internal threads threadably engages the leadscrew 152 and may be driven by a drive wheel 156 via a clutch mechanism 160.

When the reservoir 130 is empty (FIGS. 11 and 12), the plunger 136 is positioned at one end of the reservoir 130 such that the plunger 136 is extended and the clutch mechanism 160 is disengaged. In certain embodiments, the reservoir 130 may be filled with fluid, particularly insulin, by opening an inlet port to the reservoir 130 and pumping in the insulin under sufficient hydraulic pressure to retract the plunger 136 within the reservoir 130. Thereafter, the inlet port may be closed. When the reservoir 130 is filled and the plunger 136 moves to the opposite (retracted) end of the reservoir 130 (FIG. 13), the clutch mechanism 160 remains disengaged to allow the tube nut 154 to pass into an elongated cylindrical bore (along the drive axis) of a hub of the drive wheel 156. The clutch mechanism 160 may then be engaged (FIGS. 14-16) such that rotation of the drive wheel 156 causes the clutch mechanism 160 to rotate the tube nut 154, which causes the leadscrew 152 to advance the plunger into the reservoir 130 to deliver the fluid from the reservoir 130. In alternative embodiments, the reservoir 130 may be filled when the plunger 136 is already retracted.

Figure 11:
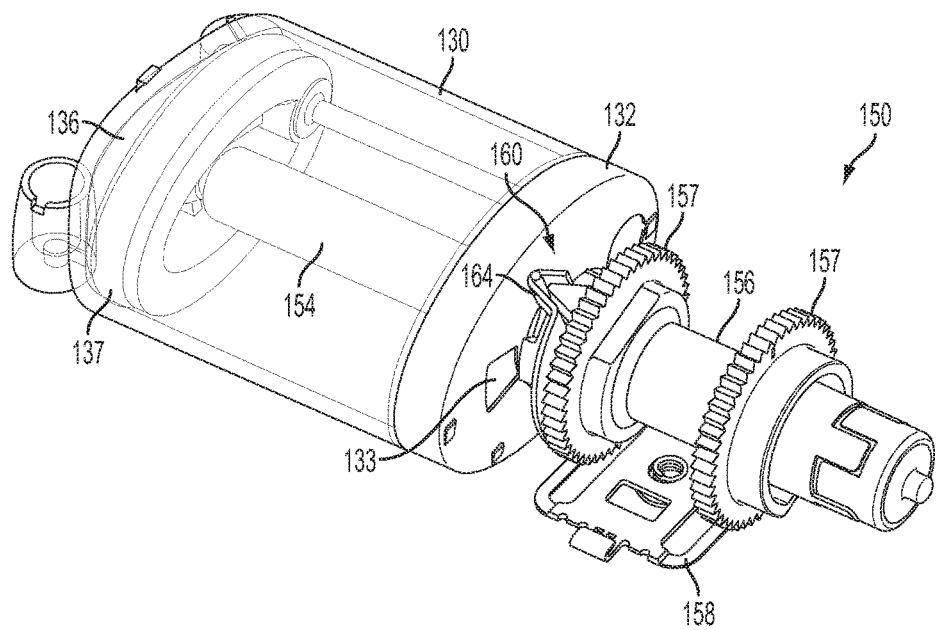
FIG. 11 is a top perspective view of a fluid driving mechanism of the fluid delivery device shown in FIG. 1 with a clutch mechanism in a disengaged position prior to filling.
Figure 12:
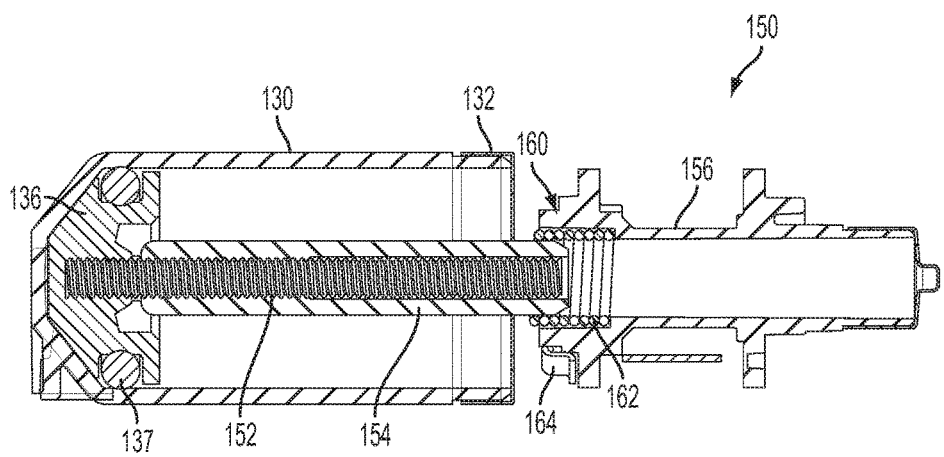
FIG. 12 is a side cross-sectional view of the fluid driving mechanism shown in FIG. 11.
Figure 13:
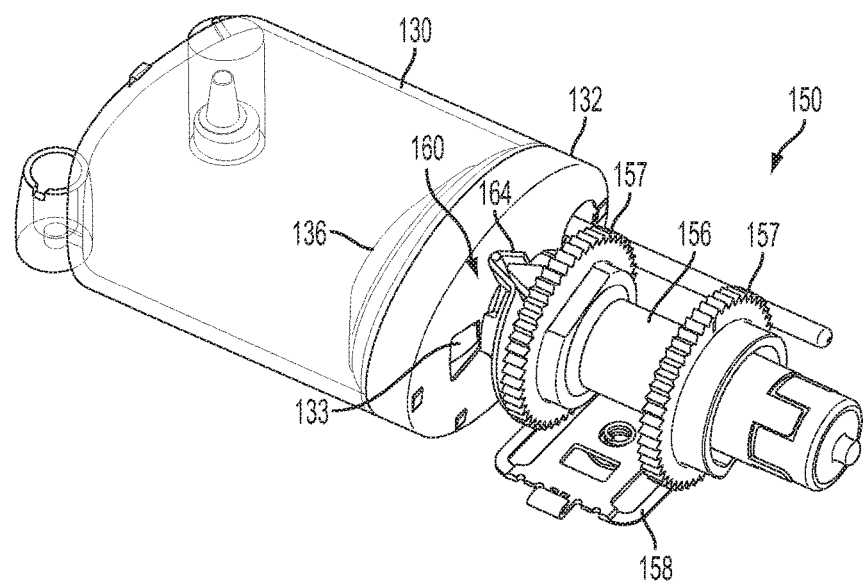
FIG. 13 is a top perspective view of the fluid driving mechanism shown in FIG. 11 with the clutch mechanism in a disengaged position after filling.
Figure 14:
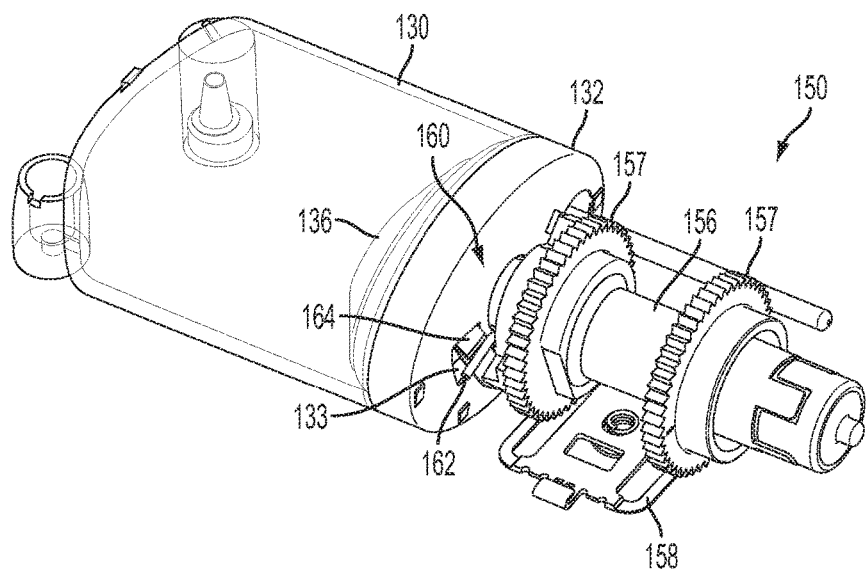
FIG. 14 is a top perspective view of the fluid driving mechanism shown in FIG. 11 with the clutch mechanism being released to the engaged position.
Figure 15:
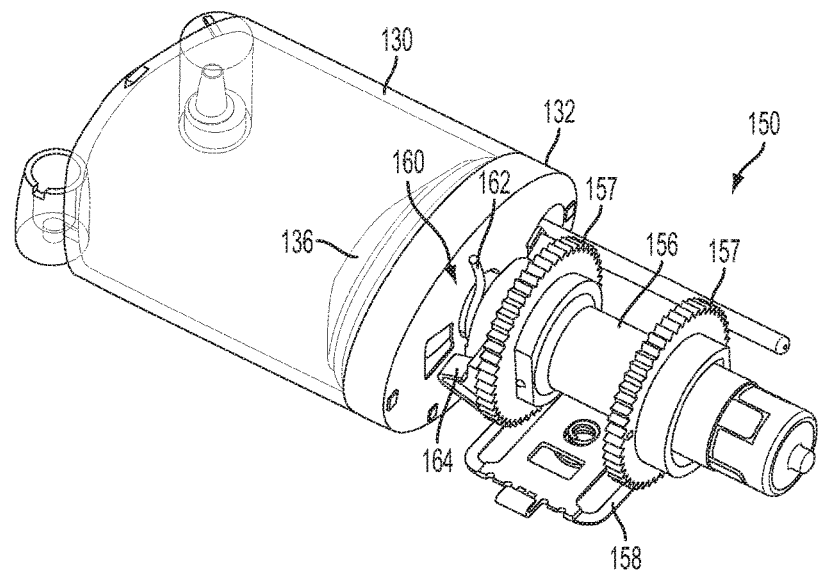
FIGS. 15 and 16 are top perspective views of the fluid driving mechanism shown in FIG. 11 with the clutch mechanism in the engaged position.
Figure 16:
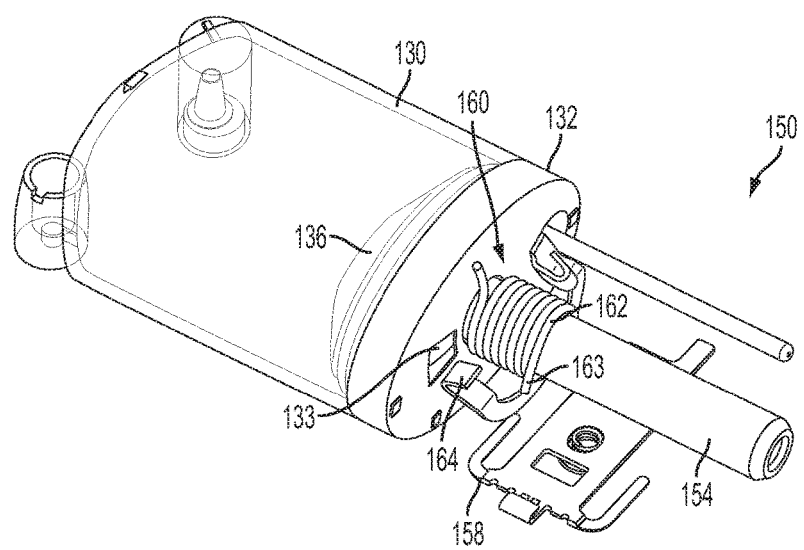
Figure 17:
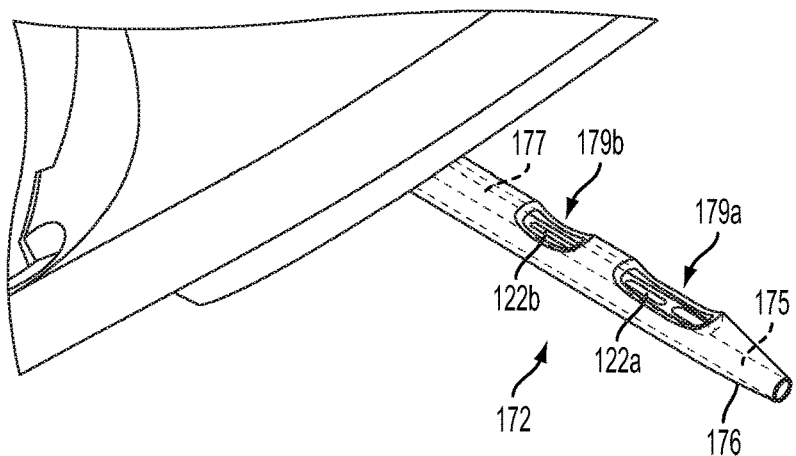
FIGS. 17-23 are views of a bi-lumen cannula used in the fluid delivery device shown in FIGS. 1-6 to insert a monitor test strip transcutaneously.
Figure 18:
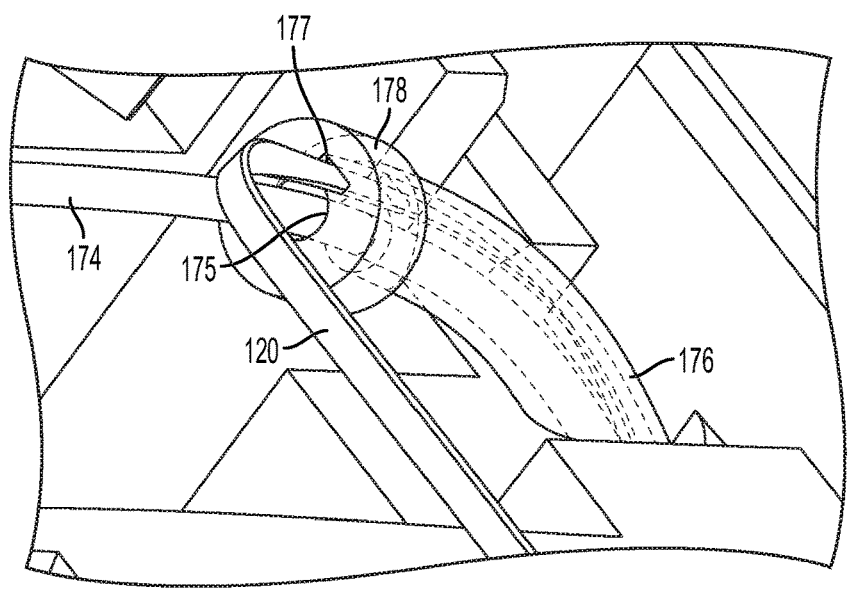
Figure 19:
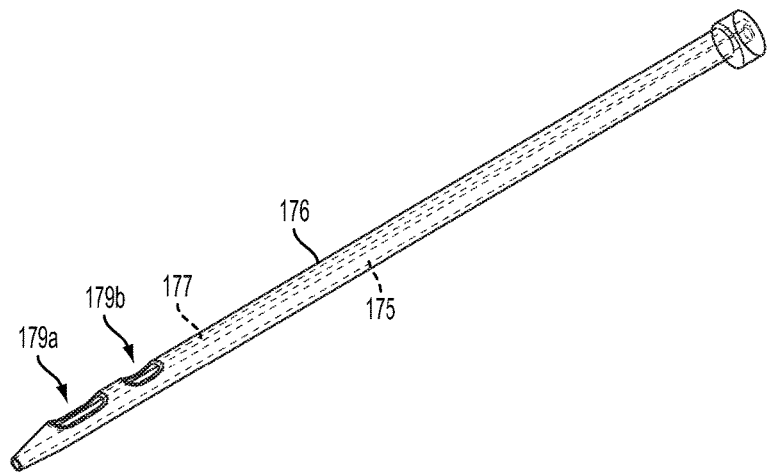
Figure 20:
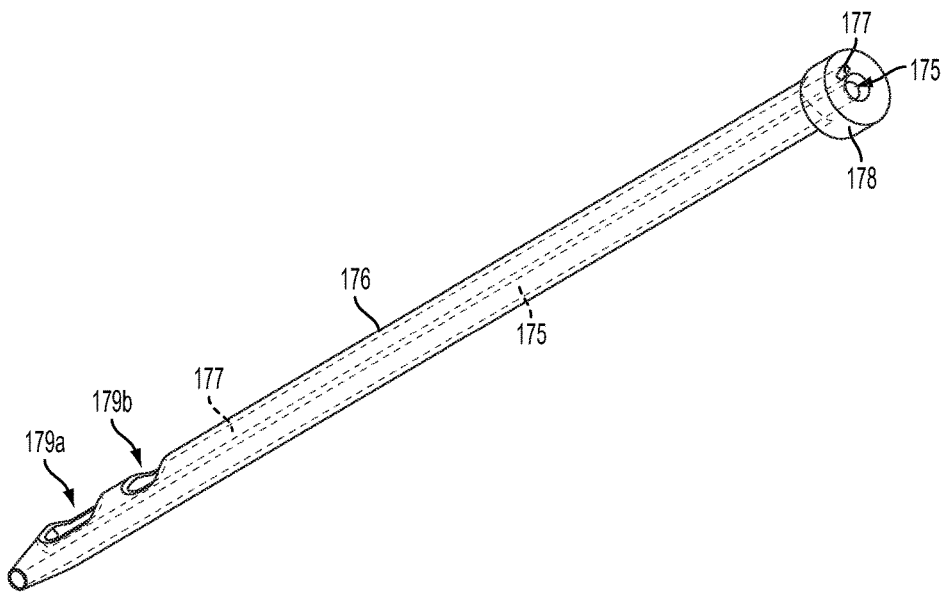
Figure 21:
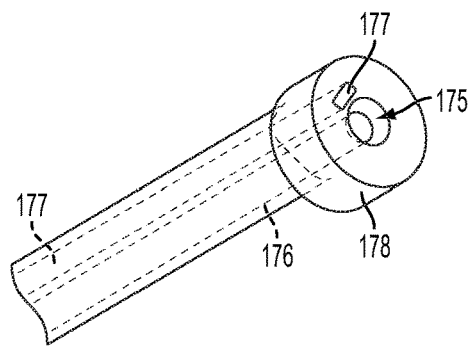
Figure 22:
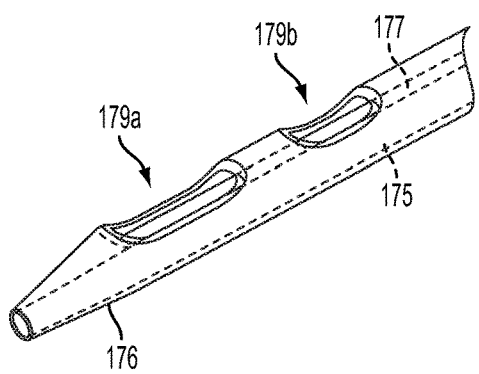
Figure 23:
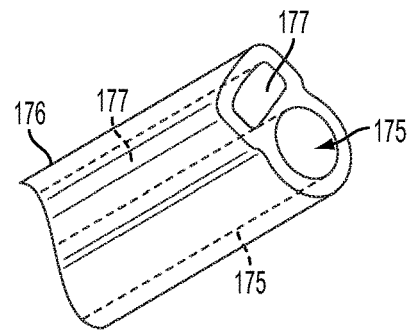
Figure 24:
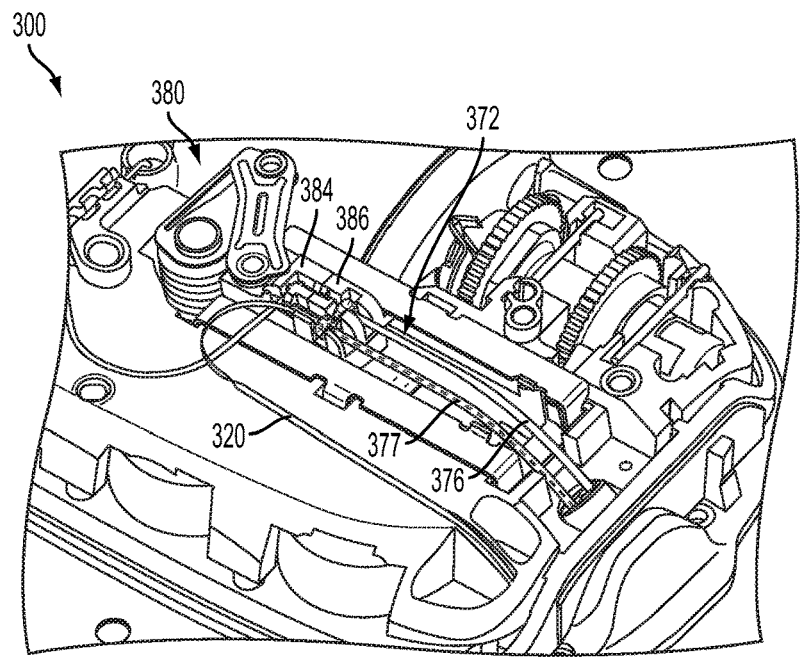
FIGS. 24-29 are views of another embodiment of a fluid delivery device including a cannula with a D-shaped lumen for inserting a monitor test strip transcutaneously.
Figure 25:
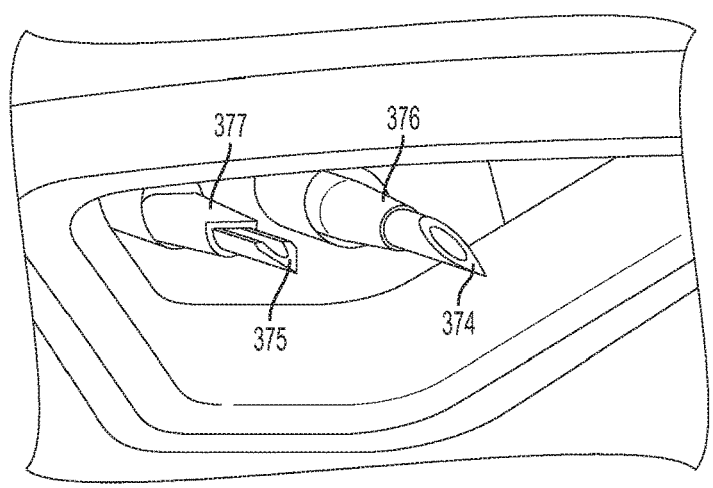
Figure 26:
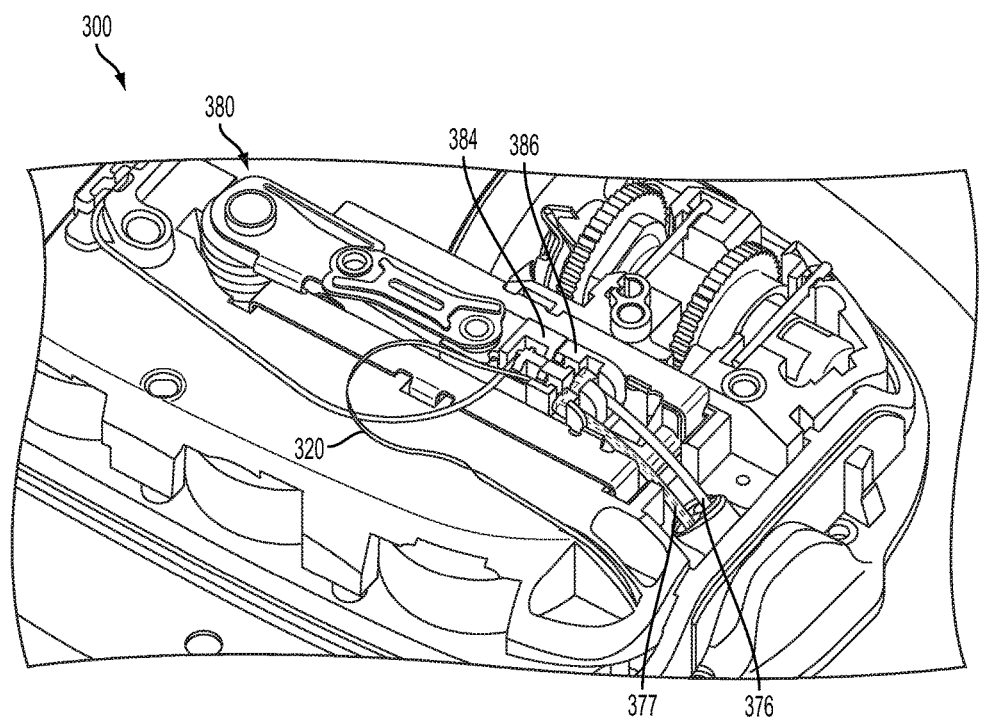
Figure 27:
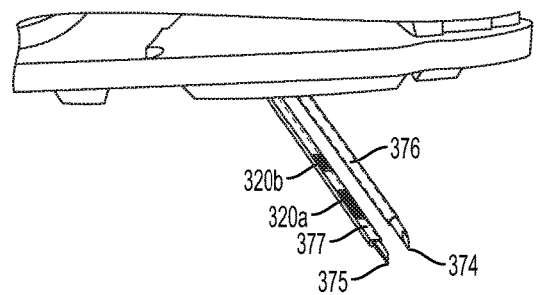
Figure 28:
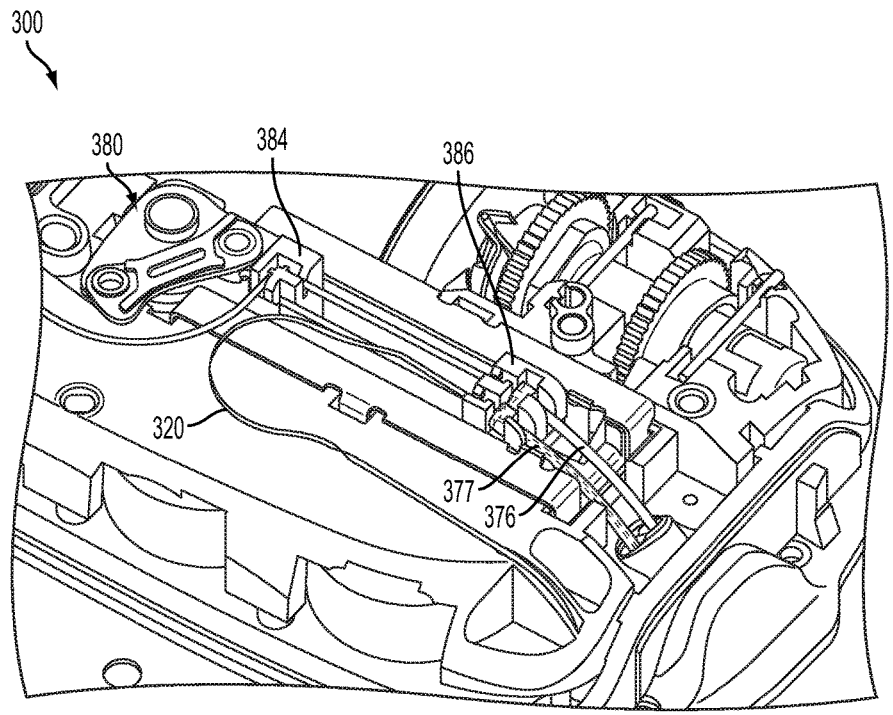
Figure 29:
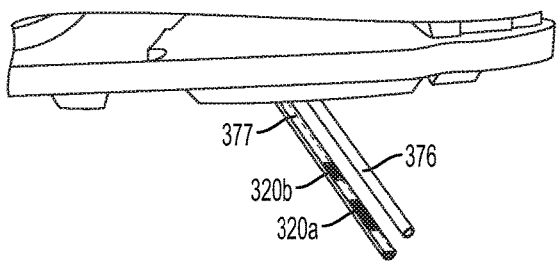
Figure 30:
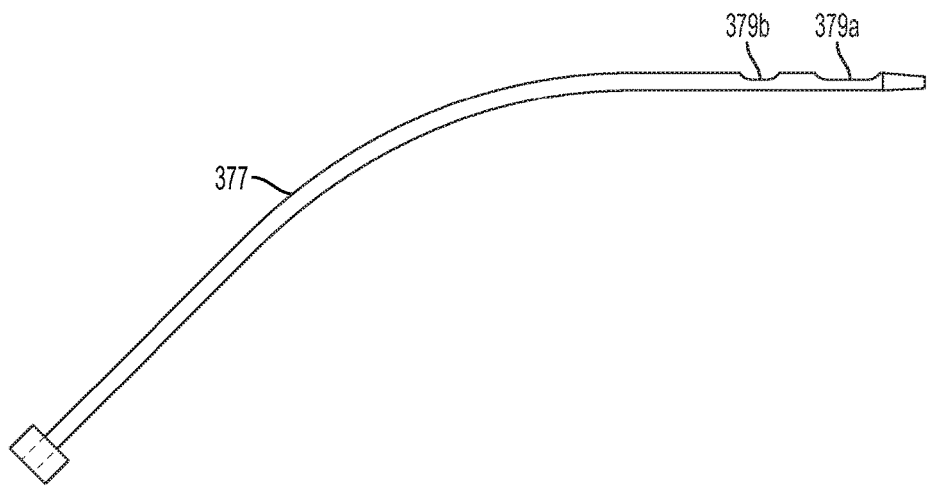
FIGS. 30-32 are views of the D-lumen cannula used in the fluid delivery device of FIGS. 24-29.
Figure 31:
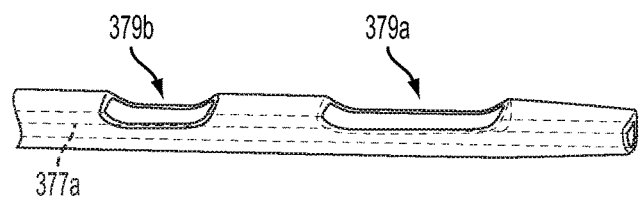
Figure 32:
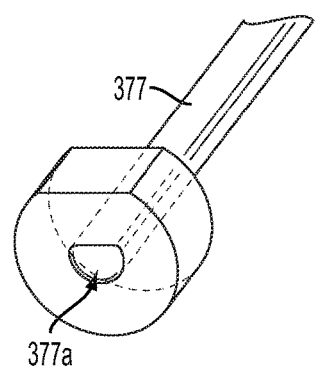
Figure 33:
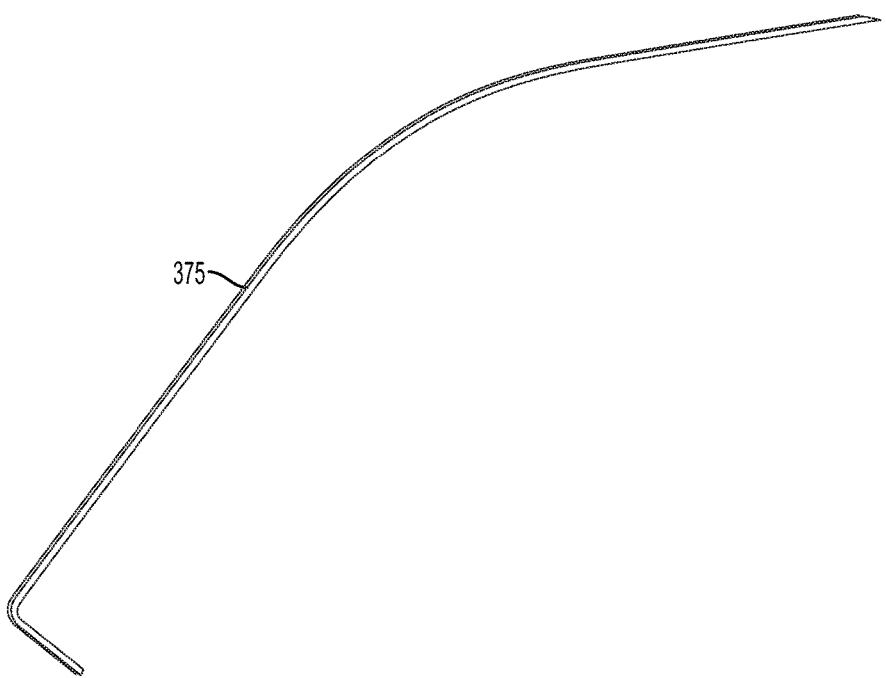
FIGS. 33 and 34 are views of a semi-circular trocar used with the D-lumen cannula in the fluid delivery device of FIGS. 18-23.
Figure 34:
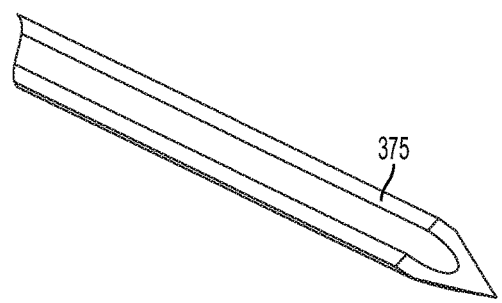
Figure 35:
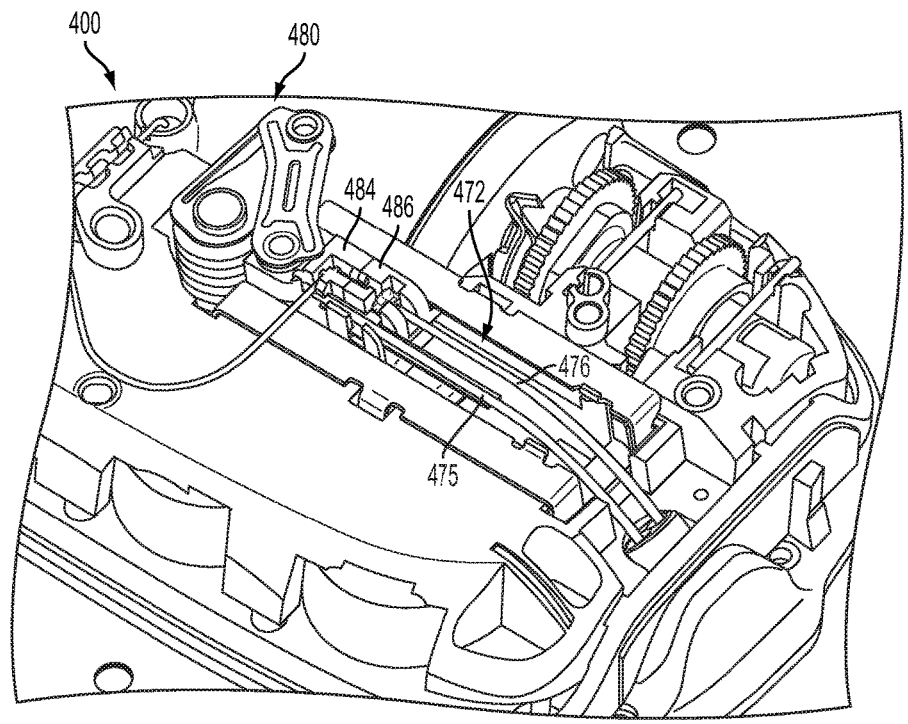
Figure 36:
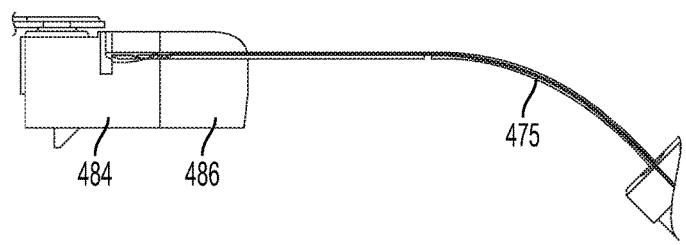
Figure 37:
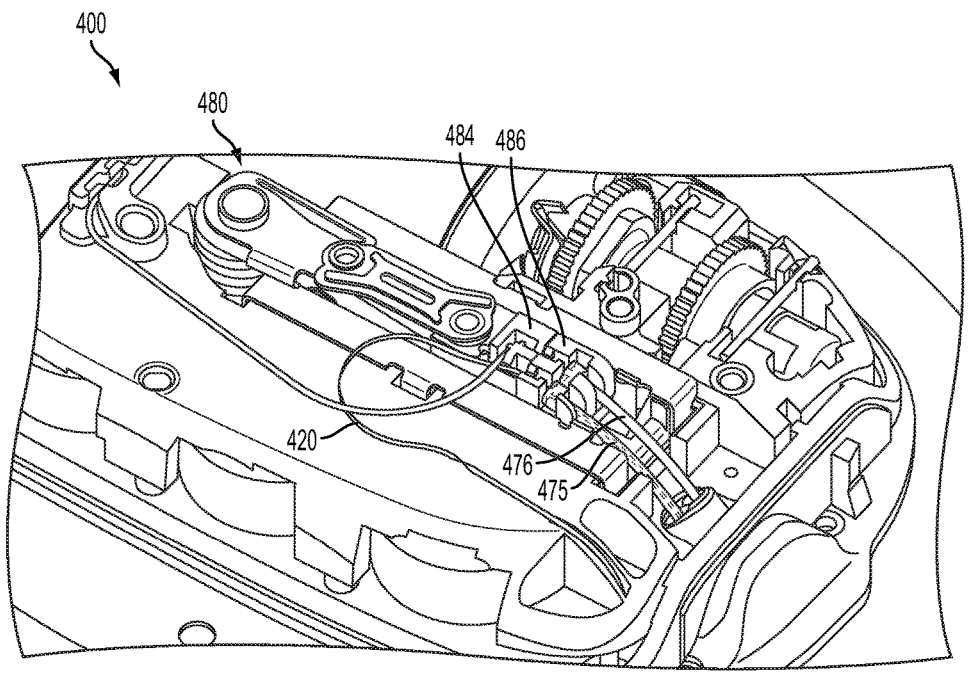
Figure 38:
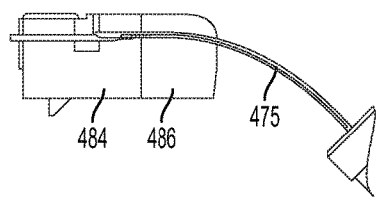

In the illustrated embodiment, the clutch mechanism 160 includes a clutch spring 162 (e.g., a helical torsion spring) located in a counterbore at one end of the drive wheel 156, adjacent the reservoir 130. The inside diameter of the clutch spring 162 is larger than the outside diameter of the tube nut 154 when the clutch spring 162 is loaded, thereby disengaging the clutch spring 162 from the tube nut 154 and allowing the tube nut 154 to pass through the center aperture of the spring 162 and into the elongated bore of the drive wheel 156. Alternatively, the inside diameter of the clutch spring 162 is smaller than the outside diameter of the tube nut 154 when the clutch spring 162 is unloaded, thereby engaging or gripping the tube nut 154 and allowing the drive wheel 156 to rotate the tube nut 154. In the illustrated embodiment, prior to filing the reservoir 130, the clutch spring 162 is held in the loaded, disengaged position by a spring latch 164 engaged with the drive wheel 156 (FIGS. 11-13). After the reservoir 130 has been filled, the clutch spring 162 may thus be engaged by rotating the drive wheel 156 until the spring latch 164 releases the clutch spring 162 (FIG. 14) allowing the clutch spring 162 to unload and grip the tube nut 154 (FIGS. 15 and 16), at which time fluid may be dispensed from the reservoir 130 with continued rotation of the drive wheel 156.

As shown, the spring latch 164 may be biased by the clutch spring 162 such that as the drive wheel 156 rotates the spring latch 164 moves rotationally against a surface of a reservoir cap 132 until clutch spring 162 deflects the spring latch 164 into a window 133 in the reservoir cap 132. When the spring latch 164 moves into the window 133, the end of the clutch spring 162 held by the spring latch 164 is released, thus engaging the clutch mechanism 160. When the clutch spring 162 is engaged, the drive wheel 156 contacts an end 163 of the clutch spring 162 to create a thrust on the clutch spring 162 that causes the clutch spring 162 to rotate the tube nut 154. The fluid drive mechanism 150 may also use other clutch mechanisms capable of allowing the tube nut 154 or other type of nut or threaded member to pass through the clutch mechanism and then being activated to engage the nut or threaded member.

In the illustrated embodiment, the drive wheel 156 includes ratchets 157 that are engaged by an actuator 158 to incrementally drive the wheel 156 and advance the plunger 136 into the reservoir 130. Examples of this actuation mechanism are described in greater detail in U.S. Patent Application Publication No. 2005/0238507, which is fully incorporated herein by reference.

By using a clutch mechanism, the engagement between the leadscrew and the nut occurs at assembly, and thus no rotation is needed for the nut to engage the leadscrew by operation of the device. This reduces the number of fluid path prime pulses to prime the pump and assures a full and proper priming of the fluid path before placement on the body. The clutch mechanism also enables the changing of thread pitch for other drug applications without a need to redesign the tilt nut used in fluid driving mechanisms in other existing pumps. The components of the clutch mechanism are also more easily inspected than the tilt nut assembly.

According to one embodiment, as shown in FIGS. 17-23, the cannula 176 providing the transcutaneous access for delivery the fluid may also be used to introduce the monitor test strip 120. In this embodiment, the cannula 176 includes a first lumen 175 for receiving the needle/trocar 174 and a second lumen 177 for receiving the test strip 120. As shown, the first lumen 175 has a circular (cylindrical) profile and the second lumen 177 has a rectangular profile. The cannula 176 may also include one or more windows 179a, 179b providing access to one or more sensors 122a, 122b on the test strip 120. As shown, the plurality of windows 179a, 179b of the cannula 176 may be arranged on a same side of the sidewall of cannula 176, with the first window 179a arranged at a distance from the distal end tip of the cannula 176 which is less than the distance of the second window 179b from the distal end tip of the cannula 176.

To insert the test strip 120 into second lumen 177, the test strip 120 passes into second lumen 177 at the head 178 of the cannula 176 and extends to the window(s) 179a, 179b. Thus, at least one window 179a, 179b exposes a sensor 122a, 122b of the monitoring test strip 120. In the example embodiment, two windows 179a, 179b are provided with the window 179a closest to the tip of the cannula 176 providing access to the main sensor area and the window 179b farthest from the tip providing a reference. Although a specific shape and configuration of a bi-lumen cannula is shown, other configurations of a cannula with first and second lumens may also be used to both deliver a therapeutic fluid and introduce a test strip subcutaneously.

According to another embodiment, as shown in FIGS. 24-34, a host fluid (medication) delivery device 100b may include a transcutaneous access tool 372 with a first cannula 376 for delivering fluid and a second cannula 377 for introducing a test strip 320. The first cannula 376 receives a first needle/trocar 374 (shown as a circular needle) to facilitate insertion of the first cannula 376 and the second cannula 377 receives a second needle/trocar 375 (shown as a semi-circular trocar) to facilitate insertion of the second cannula 377. The host fluid (medication) deliver device 100b includes an insertion mechanism 380, similar to the first described embodiment above, but with sliding members 384, 386 coupled to both the needle 374 and the trocar 375 and both cannulas 376, 377. The insertion mechanism 380 inserts the second cannula 377 and the trocar 375 and then retracts the trocar 375 in the same manner as described above. The test strip 320 remains inserted after the trocar 375 is retracted. Thus, both the first needle/trocar 374 and the second needle/trocar 375 may be introduced into the host simultaneously, particularly to reduce the pain of sequential insertions.

Similar to the above described embodiment, first cannula 376 includes a circular (cylindrical) lumen 376a. As shown in greater detail in FIGS. 30-32, the second cannula 377 includes a semi-circular (D-shaped) lumen 377a to allow the monitor strip to sit relatively flat within the cannula 377. The second cannula 377 also includes one or more windows 379a, 379b providing access to one or more sensors 320a, 320b on the test strip 320 (see FIGS. 27 and 29). As shown, similar to the prior embodiment, the plurality of windows 379a, 379b, of the cannula 377 may be arranged on a same side of the sidewall of the cannula 377, with the first window 379a arranged at a distance from the distal end tip of the cannula 377 which is less than the distance of the second window 379b from the distal end tip of the cannula 377. Thus, at least one window 379a, 379b exposes a sensor 320a, 320b of the monitoring test strip 320. In the example embodiment, two windows 379a, 379b are provided with the window 379a closest to the tip of the cannula 377 providing access to the main sensor area and the window 379b farthest from the tip providing a reference. As shown in greater detail in FIGS. 33 and 34, the trocar 375 has a shape corresponding to the D-shaped lumen 377a to allow the trocar 375 to be retracted leaving the test strip 320 inserted (see FIG. 29). As shown, the trocar includes a planar side surface 373 which corresponds to a planar test strip 320 such that, when assembled, the planar test strip 320 may be located adjacent the planar side surface 373 of the trocar 375 in the second cannula 377.

According to another embodiment, as shown in FIGS. 35-43, a host fluid (medication) delivery device 100c may include a transcutaneous access tool 472 with a cannula 476 for delivering fluid and a needle or trocar 475 (shown as a semi-circular trocar) for introducing a test strip 420. The cannula 476 receives a needle/trocar 474 (shown as circular needle) to facilitate insertion of the cannula 476 and the trocar 475 is inserted with the test strip 420. The host fluid (medication) delivery device 100c includes an insertion mechanism 480, similar to the first described embodiment above, but with sliding members 484, 486 coupled to both the needle 474 and the trocar 475. The insertion mechanism 480 inserts the trocar 475 (FIGS. 37 and 38) and then retracts the trocar 475 (FIGS. 39 and 40) in the same manner as the needle/trocar described above. The test strip 420 remains inserted after the trocar 475 is retracted (FIG. 41). In contrast to the prior embodiment, the needle/trocar 475 introduces the monitoring test strip 420 subcutaneously solely (i.e. without the monitoring test strip 420 being introduced with a cannula).

Figure 42:
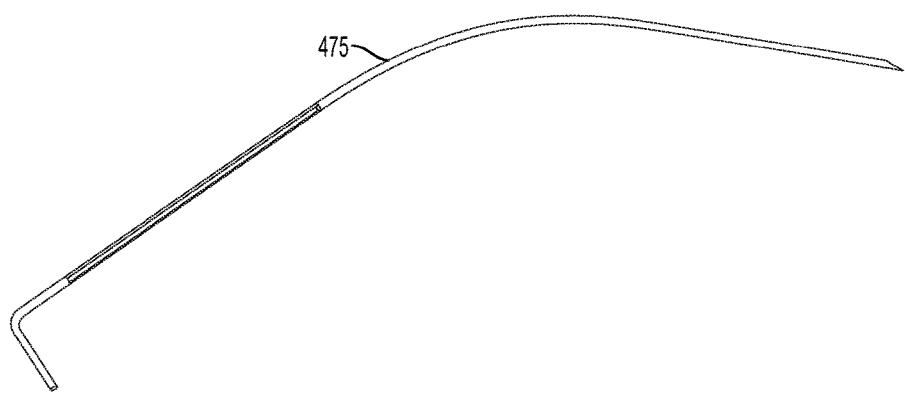
FIG. 42 is a side view of the oval trocar for use in the fluid delivery device shown in FIGS. 35-41.
Figure 43:
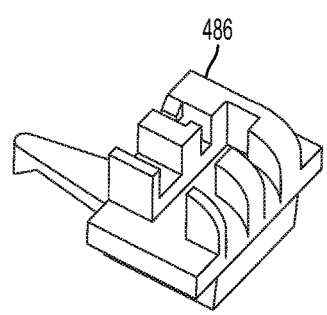
FIG. 43 is a top perspective view of a second sliding member for use in the fluid delivery device shown in FIGS. 35-41.

The trocar 475 is shown in greater detail in FIG. 42. The second sliding member 486 is shown in greater detail in FIG. 43. In this embodiment, the second sliding member 486 is designed to capture the cannula 476 and to receive and allow the trocar 475 to pass through.

Accordingly, various embodiments of the fluid delivery device may use the transcutaneous access tool both to deliver fluid and to introduce a test strip subcutaneously to provide integrated monitoring.

Figure 44:
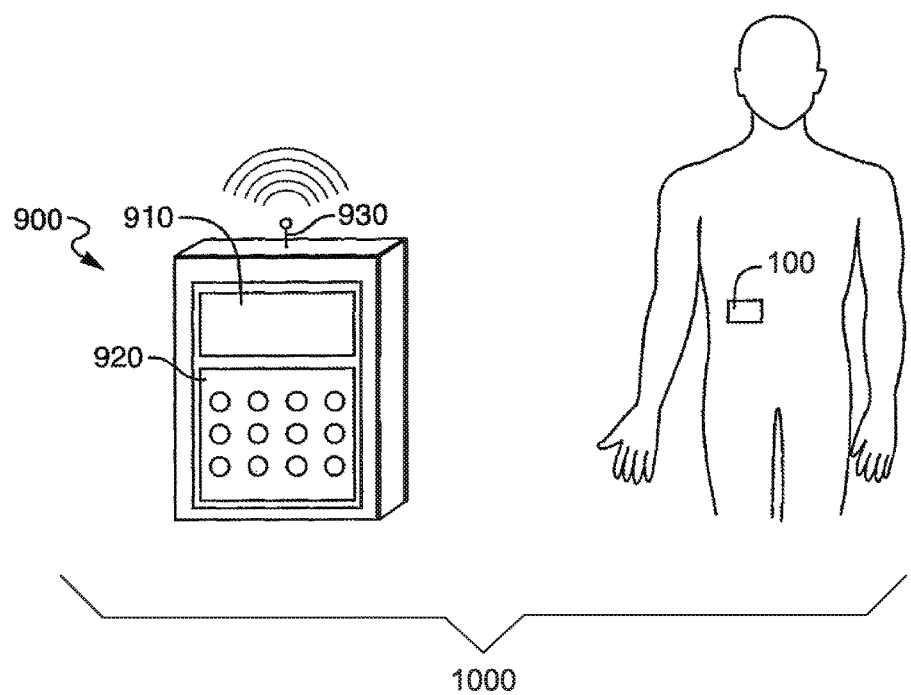
FIG. 44 is a perspective view of a fluid delivery device according to the present disclosure in conjunction with a remote control device.

As shown in FIG. 44, host fluid (medication) delivery device 100a, 100b or 100c, collectively referred to as host fluid (medication) delivery device 100) as disclosed herein may be operable, and more particularly controlled, with a separate host remote control device 900. The host fluid (medication) delivery device 100 and the separate host remote control device 900 may be components of a host treatment apparatus 1000.

The microprocessor of host fluid (medication) delivery device 100, which may be hereinafter referred to as a local (host) processor, may be programmed to cause the transcutaneous access tool insertion mechanism 180, 380 or 480 of each host fluid (medication) delivery device 100a, 100b or 100c, respectively, to deploy the transcutaneous access tool 172, 372 or 472 therein based on instructions stored on the host fluid (medication) delivery device 100 or instructions (signals) received from the host remote control device 900. The local processor may also be programmed to control delivery of the medication from the fluid reservoir 130 based on instructions stored on the host fluid (medication) delivery device 100, or instructions (signals) received from the host remote control device 900.

The host fluid (medication) delivery device 100 may receive the instructions via a wireless communication element, which thereafter provides the instructions to the local processor. In the foregoing manner, the host fluid (medication) delivery device 100 may be free of input components for providing instructions to the local processor, such as electromechanical switches or buttons on the housing 104, or interfaces otherwise accessible to a host to locally operate the host fluid (medication) delivery device 100. The lack of input components allows the size, complexity and costs of the host fluid (medication) delivery device 100 to be substantially reduced so that the host fluid (medication) delivery device 100 lends itself to being small and disposable in nature, while the remote control device 900 may be reusable.

Referring to FIG. 44, the host remote control device 900 has input components, including an array of electromechanical switches, such as the membrane keypad 920 as shown. The host remote control device 900 also includes output components, including a visual display, such as a liquid crystal display (LCD) 910. Alternatively, the host remote control device 900 can be provided with a touch screen for both input and output. Although not shown in FIG. 44, the host remote control device 900 has its own processor (hereinafter referred to as the "host remote control" processor) connected to the membrane keypad 920 and the display 910. The host remote control processor may receive the inputs from the membrane keypad 920 and provide instructions to the host fluid (medication) delivery device 100, as well as provide information to the display 910. Since the host remote control device 900 includes a visual display 910, the host fluid (medication) delivery device 100 can be void of an information screen, further reducing the size, complexity and costs of the host fluid (medication) delivery device 100.

The communication element of host fluid (medication) delivery device 100 may particularly transmit and receive electronic communication from the host remote control device 900 using radio frequency or other wireless communication standards and protocols. As such, it should be understood that the communication element of host fluid (medication) delivery device 100 may particularly be a two-way communication element for allowing the host fluid (medication) delivery device 100 to communicate with the host remote control device 900. In such an embodiment, the host remote control device 900 also includes a two-way communication element which may also comprise a receiver and a transmitter, such as a transceiver, for allowing the host remote control device 900 to transmit and receive the information sent by the host fluid (medication) delivery device 100. Specific instructions communicated to the sensors 122a, 122b of the test strip 120 may include a time schedule for taking samples and determining specific levels of glucose concentration of the host that warrant either a warning or an infusion of medication, or both.

Thus, in addition to being programmed to receive and perform instructions from the host remote control device 900, the host fluid (medication) delivery device 100 may transmit data (signals) via the transceiver back to the host remote control device 900, particularly from the one or more sensors 122a, 122b of the glucose test strip 120. Accordingly, the host fluid (medication) delivery device 100 may be used to measure glucose concentration level, in situ, and, optionally, to control the delivery of the medication to the host based on the data.

Alternatively, the host fluid (medication) delivery device 100 may include an interface, including various input and information displaying components built into the housing 104, thus providing a unitary sensing device which does not require the use of a separate host remote control device 900.

Thus, host fluid (medication) delivery device 100 and optionally the host remote control device 900 may contain all the computer programs and electronic circuitry needed to allow a host to program the desired flow patterns and rates, and adjust the program(s) as necessary. Such circuitry may include one or more microprocessors, digital and analog integrated circuits, resistors, capacitors, transistors and other semiconductors and other electronic components known to those skilled in the art. Furthermore, host fluid (medication) delivery device 100 and optionally the host remote control device 900 may contain all the computer programs and electronic circuitry needed to allow a host to activate one or more sensors 122a, 122b of the glucose test strip 120.

Thus, with the incorporation of glucose test strip 120, the host fluid (medication) delivery device 100 may be programmed to monitor glucose concentration level of a host at particular times during the day, without the finger pricking associated with host dependent (self monitoring) of glucose concentration level.

Host fluid (medication) delivery device 100 may also apply a host specific insulin diffusion profile for a predetermined time period during which time the host fluid (medication) delivery device 100 is programmed to operate with an algorithm which may be specifically configured to the specific host. Host fluid (medication) delivery device 100 may be programmed to compare a measured glucose value, as determined with the sensors 122a, 122b, to a targeted glucose concentration level provided by the algorithm. The algorithm may provide a predetermined tolerance range for the glucose concentration level as a function a time. If at any given time the glucose concentration level has measured by the sensors 122a, 122b is outside the tolerance range established by the algorithm, the host fluid (medication) delivery device 100 may emit a warning to the host that the glucose concentration level is too low or too high.

In addition, with host fluid (medication) delivery devices 100 disclosed herein, it may be confirmed that the medication has been actually delivered to the host of the host fluid (medication) delivery device 100 by measuring a physiological parameter associated with the tissue into which the medication is delivered, particularly within a predetermined time period after delivery of the medication.

Figure 45:
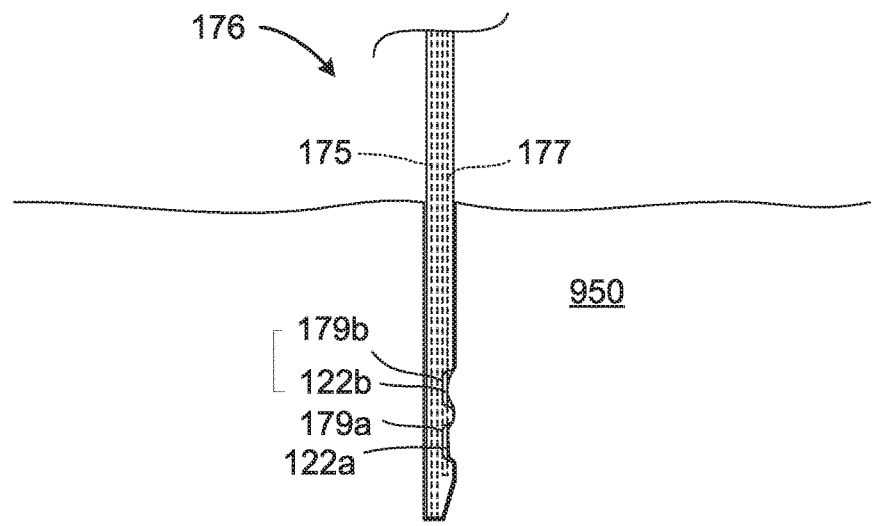
FIG. 45 is a side view of a cannula according to the present disclosure within tissue before delivery of medication.

Referring now to FIG. 45, there is shown cannula 176 inserted in tissue 950 after being delivered by needle 174. As shown, the tissue 950, and more particularly the fluid thereof, is adjacent and in contact with sensors 122a, 122b.

Thereafter, before host fluid (medication) delivery device 100 is to inject insulin, and/or another therapeutic fluid, sensors 122a, 122b may be used to measure a physiological parameter, here glucose concentration level, associated with the tissue 950 adjacent thereto, which may provide a predetermined measured value of the glucose concentration level before delivering the medication. Such may be determined at a predetermined time prior to injection of the medication by the programming of host fluid (medication) delivery device 100. For convenience and the potential for increased accuracy, measurement of the glucose concentration level may be performed within a few minutes (e.g. less than 5 minutes) prior to injection of the medication, such as within 2 minutes before injection and more particularly within 1 minute before injection. Even more particularly, measurement of the glucose concentration level may be performed within 30 seconds before injection.

Sensors 122a, 122b may particularly be enzymatic sensors. The sensors 122a, 122b may be connected by wire to a memory of host fluid (medication) delivery device 100 to record data that can be stored and/or sent to host remote control device 900. The tip of the sensors 122a, 122b may be made of a membrane selectively permeable to glucose. Without being bound to a particular theory, once the glucose passes through the membrane, it may be oxidized by the enzyme glucose oxidase. Reduced glucose oxidase may then be oxidized by reacting with molecular oxygen, forming hydrogen peroxide as a by-product. At the electrode surface, hydrogen peroxide may be oxidized into water, generating a current which can be measured and correlated to the glucose concentration outside the membrane.

Thereafter, when insulin/therapeutic fluid is delivered from cannula 176 into the tissue 950 of the host, the sensors 122a, 122b may be used to detect a change of the measured glucose concentration level by sensors 122a, 122b.

Figure 46:
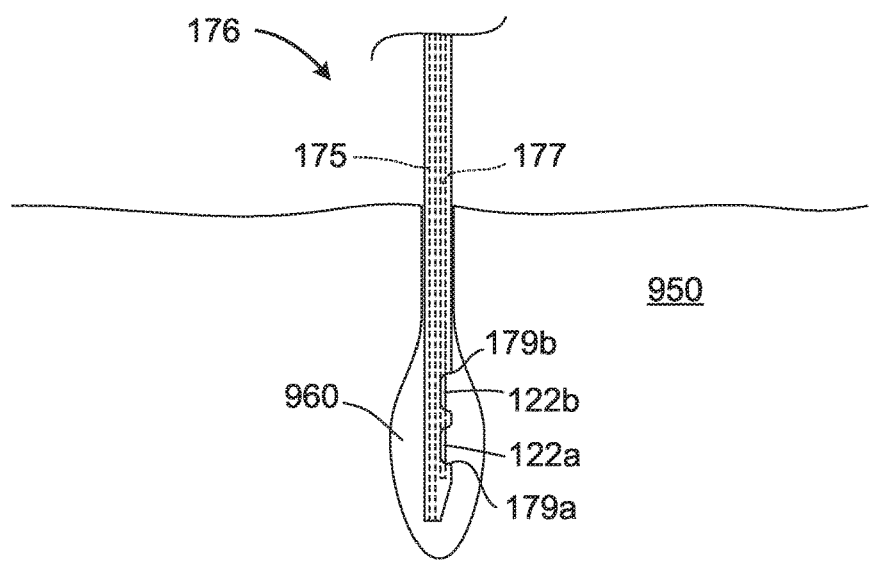
FIG. 46 is a side view of a cannula according to the present disclosure within tissue after delivery of medication.

As shown in FIG. 46, when insulin/therapeutic fluid is delivered from cannula 176 of host fluid (medication) delivery device 100, the insulin/therapeutic fluid may form a temporary depot 960 (i.e. storage) in the tissue 950 at the injection site. The size of the temporary depot 960 and the duration it will exist may be understood to depend at least on the rate of injection, the injection quantity, the type of medication (e.g. fast acting, intermediate acting, long lasting) and the type of tissue.

As shown, due to the sensors 122a, 122b being within the injection site and, more particularly, within the injection path defined by the needle 174 and cannula 176, the temporary depot 960 forms around the tip of the cannula 176, inclusive of sensors 122a, 122b.

Due to the injection pressure of the insulin/therapeutic fluid pushing the insulin/therapeutic fluid into the body, and overcoming the resistance (hydrostatic) pressure of the tissue 950, the insulin/therapeutic fluid may be understood to physically displace the tissue 950 in contact with the sensors 122a, 122b, and more particularly the fluids of the tissue 950 in contact with the sensors 122a, 122b. In doing so, the insulin/therapeutic fluid will at least partially, and more particularly completely surround and engulf the sensors 122a, 122b within the depot 960.

As the insulin/therapeutic fluid physically displaces and "washes away" the fluids in contact with the sensors 122a, 122b, the glucose concentration level being detected by the sensors 122a, 122b may be understood to change, and more particularly decrease from the pre-medication delivery measured glucose concentration level to a post-medication delivery measured glucose concentration level.

Even more particularly, when the insulin/therapeutic fluid surrounds and engulfs the sensors 122a, 122b, the glucose concentration level being detected by the sensors 122a, 122b may substantially decrease towards zero, or even may drop to zero, depending on the size of the temporary depot 960 and/or the ability of the depot 960 to displace the tissue 950 in contact with the sensors 122a, 122b.

As such, the change in glucose concentration level being detected by the sensors 122a, 122b is indicative that a temporary depot 960 has formed around the tip of the cannula 176 inclusive of sensors 122a, 122b, which has effectively displaced the glucose concentration previously detected by the sensors 122a, 122b and, as such, may be understood to confirm delivery of the insulin/therapeutic fluid from the medication delivery device to the host.

However, as set forth above, the size of the temporary depot 960 and the duration it will exist may be understood to depend on the rate of injection, as well as the injection quantity, the type of medication (e.g. fast acting, intermediate acting, long lasting) and the type of tissue. As such, the post-medication delivery measured glucose concentration level to confirm insulin/therapeutic fluid delivery must be measured within a predetermined time period, particularly after injection has terminated, by the programming of host fluid (medication) delivery device 100.

The length of the predetermined time period will depend on how long the temporary depot 960 may exist before the temporary depot 960 is completely absorbed into tissue 950 and the tissue 950 (e.g. extracellular fluid such as interstitial fluid) reestablishes contact with the sensors 122a, 122b where the depot 960 was located. In other words, immediately following injection of the insulin/therapeutic fluid, the injected insulin/therapeutic fluid may be expected to begin to be absorbed and dissipate into the interstitial space between the adjacent cells of the tissue 950. Such may also involve displacing extracellular fluid, such as the interstitial fluid, in the interstitial space between the cells. As the insulin/therapeutic fluid flows and dissipates into the interstitial space, the insulin/therapeutic fluid and the size of the depot 960 will decrease. As such, the existence of the temporary depot 960, and the corresponding time period for measuring the post-medication delivery measured glucose concentration level, may only last for several minutes, or for less than a minute, depending on the foregoing factors.

Thus, the time period to detect and measure the post-medication delivery measured glucose concentration level may be in a range between 0.1 second to 10 minutes (600 seconds), particularly after injection has terminated. In other embodiments, the time period may be in a range between 0.1 second to 9 minutes (540 seconds); 0.1 second to 8 minutes (480 seconds); 0.1 second to 7 minutes (420 seconds); 0.1 second to 6 minutes (360 seconds); 0.1 second to 5 minutes (300 seconds); 0.1 second to 4 minutes (240 seconds); 0.1 second to 3 minutes (180 seconds); 0.1 second to 2 minutes (120 seconds); 0.1 second to 1 minute (60 seconds); 0.1 second to 55 seconds; 0.1 second to 50 seconds; 0.1 second to 45 seconds; 0.1 second to 40 seconds; 0.1 second to 35 seconds; 0.1 second to 30 seconds; 0.1 second to 25 seconds; 0.1 second to 20 seconds; 0.1 second to 15 seconds; 0.1 second to 10 seconds; and 0.1 second to 5 seconds. It should also be realized that the time to detect and measure the post-medication delivery measured glucose concentration level may also be determined using the beginning of injection as the reference point for starting the relevant time period as an alternative to the time period beginning after injection has terminated.

For convenience (to reduce waiting time) and the potential for increased accuracy, the post-medication delivery measured glucose concentration level may be particularly detected and measured in a time period in a range of 0.1 second to 2 minutes (120 seconds) and more particularly in a range of 0.1 second to 1 minute (60 seconds) after injection has terminated. Even more particularly, measurement of the glucose concentration level may be performed in a range of 0.1 second to 30 seconds after injection has terminated. Such may provide confirmation that the insulin/therapeutic fluid has been delivered to the host in light of a change in glucose concentration level as measured by the sensors 122a, 122b.

In other embodiments, a response from the sensors 122a, 122b may be turned off or otherwise discarded for a short time period after obtaining the pre-medication delivery measured glucose concentration level, and more particularly during or after delivery of the insulin/therapeutic fluid from cannula 176 of host fluid (medication) delivery device 100. Such may be performed during the transient period while the insulin/therapeutic fluid physically displaces and "washes away" the fluids in contact with the sensors 122a, 122b. As such, a delay period for obtaining the post-medication delivery measured glucose concentration level, either after obtaining the pre-medication delivery measured glucose concentration level or after delivery of the insulin/therapeutic fluid from cannula 176 of host fluid (medication) delivery device 100, maybe in a range between 0.1 second to 1 minute (60 seconds); 0.1 second to 55 seconds; 0.1 second to 50 seconds; 0.1 second to 45 seconds; 0.1 second to 40 seconds; 0.1 second to 35 seconds; 0.1 second to 30 seconds; 0.1 second to 25 seconds; 0.1 second to 20 seconds; 0.1 second to 15 seconds; 0.1 second to 10 seconds; and 0.1 second to 5 seconds. After the delay period has expired, the sensors 122a, 122b may then be used to detect and measure the post-medication delivery measured glucose concentration level within the timer period as set forth above.

Once a post-medication delivery measured glucose concentration level has been obtained which is indicative that the insulin/therapeutic fluid has been delivered to the host, the sensors 122a, 122b may be used to continue to monitor glucose concentration level as the glucose concentration level rises back towards normal ranges, or the sensors 122a, 122b may be turned off for a predetermined period of time during which the depot 960 may be expected to have been absorbed.

Alternatively, in other embodiments, such as a situation where glucose is injected, for example, to counter act the effects of an insulin injection, the glucose concentration level being detected by the sensors 122a, 122b may be understood to change, and more particularly increase from the pre-medication delivery measured glucose concentration level to a post-medication delivery measured glucose concentration level.

Even more particularly, when the injected glucose surrounds and engulfs the sensors 122a, 122b, the glucose concentration level being detected by the sensors 122a, 122b may substantially increase above the pre-medication delivery measured glucose concentration level, depending on the size of the temporary depot 960 and/or the ability of the depot 960 to displace the tissue 950 in contact with the sensors 122a, 122b.

Again, the change in glucose concentration level being detected by the sensors 122a, 122b is indicative that a temporary depot 960 has formed around the tip of the cannula 176 inclusive of sensors 122a, 122b, which has effectively displaced the glucose concentration previously detected by the sensors 122a, 122b and, as such, may be understood to confirm delivery of the glucose injection from the medication delivery device to the host.

Once a post-medication delivery measured glucose concentration level has been obtained which is indicative that the glucose has been delivered to the host, the sensors 122a, 122b may be used to continue to monitor glucose concentration level as the glucose concentration level lowers back towards normal ranges, or the sensors 122a, 122b may be turned off for a predetermined period of time during which the depot 960 may be expected to have been absorbed.

Thus, the foregoing description provides a method of treating a host with a medication, with the method comprising providing a fluid (medication) delivery device 100 which delivers medication into tissue (e.g. 950) of the host, wherein the medication delivery device includes a sensor (e.g. 122a, 122b), and wherein the sensor is used to measure a physiological parameter (e.g. glucose concentration level) associated with the tissue; introducing the medication delivery device including the sensor into the tissue; delivering the medication into the tissue of the host; and confirming delivery of the medication from the medication delivery device to the host, wherein confirming delivery of the medication comprises using the sensor to measure the physiological parameter within a predetermined time period after delivery of the medication.

Furthermore, in certain embodiments confirming delivery of the medication from the fluid (medication) delivery device 100 to the host may further comprise determining a value of the physiological parameter measured before delivering the medication; determining a value of the physiological parameter measured within the predetermined time period after delivery of the medication; and determining that the value of the physiological parameter measured within the predetermined time after delivery of the medication is less than, or greater than, the value of the physiological parameter measured before delivering the medication into the tissue. Thus, based on such methodology, confirming delivery of the medication from the medication delivery device to the host would merely require the value of the physiological parameter measured within the predetermined time after delivery of the medication being less than, or greater than, the value of the physiological parameter measured before delivering the medication into the tissue.

In other embodiments, in addition to determining a value of the physiological parameter measured before delivering the medication, and determining a value of the physiological parameter measured within the predetermined time period after delivery of the medication, confirming delivery of the medication from the fluid (medication) delivery device 100 to the host may further comprise determining a numerical difference between the value of the physiological parameter measured before delivering the medication into the tissue, and the value of the physiological parameter measured within the predetermined time after delivering the medication into the tissue; providing a predetermined representative value for the numerical difference of the physiological parameter with (e.g. stored on, such as in an electronic memory thereof) the medication delivery device; and determining the numerical difference between the two measured values of the physiological parameter is greater than a predetermined representative value for the numerical difference provided by (e.g. stored on) the medication delivery device.

Thus, based on such methodology, confirming delivery of the medication from the medication delivery device to the host may require a numerical difference between the two measured values of the physiological parameter to reach a predetermined threshold of a predetermined representative value for the numerical difference provided by (e.g. stored on, such as in an electronic memory thereof) the medication delivery device before confirming delivery of the medication from the medication delivery device to the host. In such manner, confirming delivery of the medication from the medication delivery device to the host is not merely performed based on a value of the physiological parameter measured within the predetermined time after delivery of the medication being less than, or greater than, a value of the physiological parameter measured before delivering the medication into the tissue, but rather a magnitude of a numerical difference between the two measured values of the physiological parameter being significant enough to reach a predetermined threshold. In certain embodiments, the predetermined representative value for the numerical difference provided by (e.g. stored on) the medication delivery device is at least at least 20 mg/dL, and more particularly as least 30 mg/dL, or in a range of 20 mg/dL to 60 mg/dL.

In other embodiments, in addition to determining a value of the physiological parameter measured before delivering the medication, and determining a value of the physiological parameter measured within the predetermined time period after delivery of the medication, confirming delivery of the medication from the fluid (medication) delivery device 100 to the host may further comprise determining a percentage change between the value of the physiological parameter measured before delivering the medication into the tissue, and the value of the physiological parameter measured within the predetermined time after delivering the medication into the tissue; providing a predetermined representative value for the percentage change of the physiological parameter with (e.g. stored on, such as in an electronic memory thereof) the medication delivery device; and determining the percentage change between the two measured values of the physiological parameter is greater than a predetermined representative value for the percentage change provided by (e.g. stored on) the medication delivery device.

Thus, based on such methodology, confirming delivery of the medication from the medication delivery device to the host may require a percentage change between the two measured values of the physiological parameter to reach a predetermined threshold of a predetermined representative value for the percentage change provided by (e.g. stored on, such as in an electronic memory thereof) the medication delivery device before confirming delivery of the medication from the medication delivery device to the host. In such manner, confirming delivery of the medication from the medication delivery device to the host is not merely performed based on a value of the physiological parameter measured within the predetermined time after delivery of the medication being less than, or greater than, a value of the physiological parameter measured before delivering the medication into the tissue, but rather a magnitude of a percentage change between the two measured values of the physiological parameter being significant enough to reach a predetermined threshold. In certain embodiments, the predetermined representative value for the percentage change provided by (e.g. stored on) the medication delivery device is at least 15%, or more particularly at least 20%, or even more particularly at least 25%, or in a range of 15% to 75%.

In other embodiments, it may not be necessary to determining a value of the physiological parameter measured before delivering the medication. Confirming delivery of the medication from the fluid (medication) delivery device 100 to the host may comprise determining a value of the physiological parameter measured within the predetermined time period after delivery of the medication; providing a predetermined representative value for the physiological parameter with (e.g. stored on, such as in an electronic memory thereof) the medication delivery device; and determining that the measured value of the physiological parameter within the predetermined time period after delivery of the medication is less than, or greater than, the predetermined representative value for the physiological parameter provided by (e.g. stored on) the medication delivery device.

The foregoing description also provides a method of treating a host with a medication, with the method comprising providing a medication delivery device which delivers medication into tissue of the host, wherein the medication delivery device includes a sensor, and wherein the sensor is used to measure a physiological parameter associated with the tissue; introducing the medication delivery device including the sensor into the tissue such that the tissue is in contact with the sensor; delivering the medication into the tissue of the host; forming a depot in the tissue with the medication, wherein the sensor is at least partially within the depot and the depot reduces the tissue contact with the sensor; confirming delivery of the medication from the medication delivery device to the host, wherein confirming delivery of the medication comprises using the sensor to measure the physiological parameter while the sensor is within the depot.

In certain embodiments, confirming delivery of the medication from the medication delivery device to the host may further comprise determining a value of the physiological parameter while the sensor is within the depot; providing a predetermined representative value for the physiological parameter with the medication delivery device; and after delivery of the medication, determining that the measured value of the physiological parameter while the sensor is within the depot is less than, or greater than, the predetermined representative value for the physiological parameter provided by the medication delivery device.

In other embodiments, confirming delivery of the medication from the medication delivery device to the host may further comprise determining a value of the physiological parameter measured before delivering the medication; after delivery of the medication, determining a value of the physiological parameter measured while the sensor is within the depot; and determining that the value of the physiological parameter measured while the sensor is within the depot is less than, or greater than, the value of the physiological parameter measured before delivering the medication into the tissue.

In other embodiments, confirming delivery of the medication from the medication delivery device to the host may further comprise determining a value of the physiological parameter measured before delivering the medication; after delivery of the medication, determining a value of the physiological parameter measured while the sensor is within the depot; determining a numerical difference between the value of the physiological parameter measured before delivering the medication into the tissue, and the value of the physiological parameter measured while the sensor is within the depot; providing a predetermined representative value for the numerical difference of the physiological parameter with the medication delivery device; and determining the numerical difference between the two measured values of the physiological parameter is greater than a predetermined representative value for the numerical difference provided by the medication delivery device.

In other embodiments, confirming delivery of the medication from the medication delivery device to the host may further comprise determining a value of the physiological parameter measured before delivering the medication; after delivery of the medication, determining a value of the physiological parameter measured while the sensor is within the depot; determining a percentage change between the value of the physiological parameter measured before delivering the medication into the tissue, and the value of the physiological parameter measured while the sensor is within the depot; providing a predetermined representative value for the percentage change of the physiological parameter with the medication delivery device; and determining the percentage change between the two measured values of the physiological parameter is greater than a predetermined representative value for the percentage change provided by the medication delivery device.

In other embodiments, confirming delivery of the medication from the medication delivery device to the host may not always involve use of a sensor configured to measure a physiological parameter associated with tissue, such as sensors 122a, 122b of monitoring test strip 120.

Figure 47:
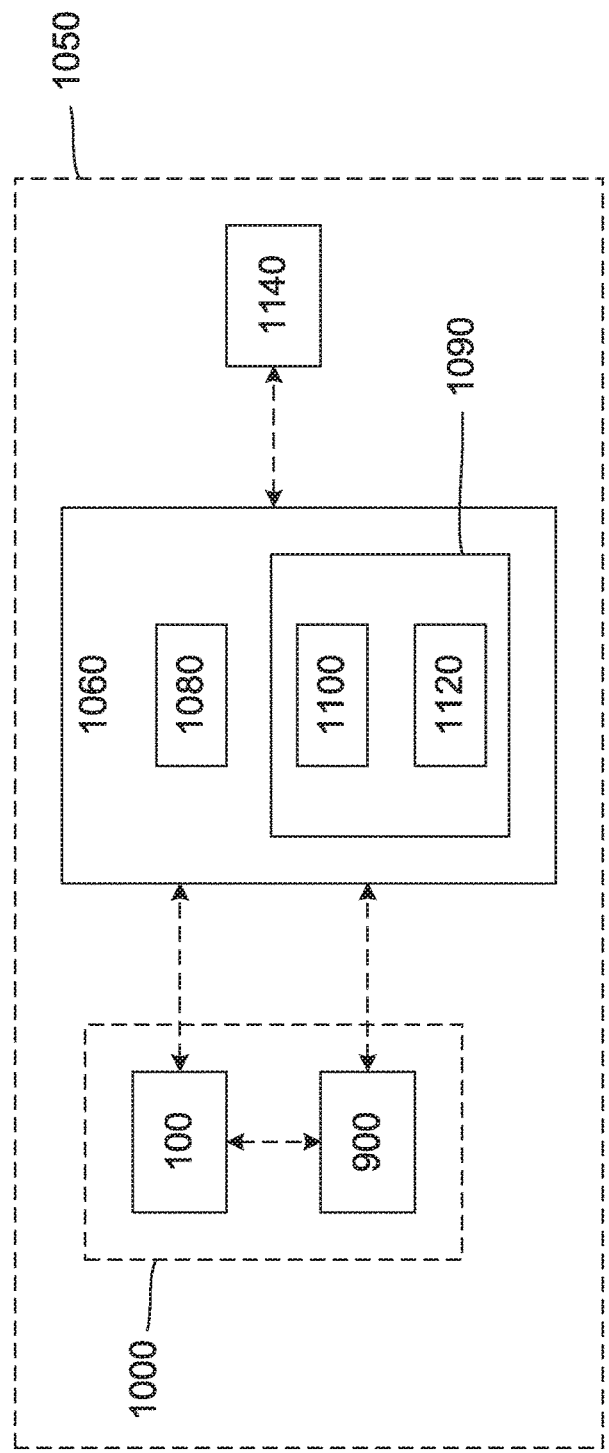
FIG. 47 is a plan view of a computer network including a host treatment apparatus.

Referring now to FIG. 47, Ii addition to, or as an alternative to, communicating with host remote control device 900, host fluid (medication) delivery device 100 may be configured to electronically communicate with a computer network 1050 comprising one or more computers 1060 (e.g. as part of a local or wide area network), which may function as remote servers, i.e. remote from the host. Moreover, the computer network 1050, and more particularly the one or more computers 1060, may commute with a plurality of host fluid (medication) delivery devices 100. Computer 1060 of computer network 1050 may be particularly used by a clinician (e.g. doctor, nurse) to communicate with host treatment apparatus 1000, i.e. host fluid (medication) delivery device 100 and optionally the host remote control device 900. Computer 1060 of computer network 1050 may be part of a desktop computer, a laptop computer, a computer tablet, a smart phone, etc.

During start-up and ongoing operation, host fluid (medication) delivery device 100 may be configured to perform a plurality (e.g. series) of operational tasks/functions in accordance with a programmed software application residing on the host treatment apparatus 1000, and more particularly host fluid (medication) delivery device 100. In addition, host treatment apparatus 1000, and more particularly the host fluid (medication) delivery device 100 may be configured to perform operational status monitoring to ensure the operational tasks/functions have been properly performed in accordance with pre-established operational procedures (e.g. programming). Moreover, host treatment apparatus 1000, and more particularly host fluid (medication) delivery device 100, may be configured to monitor and communicate its operational status, particularly with regards to successful/unsuccessful completion of one or more pre-established tasks/functions, to computer 1060 of computer network 1050.

Such may be particularly useful to monitor/confirm delivery of medication and report host medication delivery compliance. Such many be used as part of out-patient therapy by providing real time host compliance data to an internet based host monitoring system to which computer 1060 of computer network 1050 is connected and operational therewith. Clinicians may then take proactive actions to address non-compliance issues remotely and in real time.

More particularly, host fluid (medication) delivery device 100 may be configured to monitor medication delivery tasks/functions and related operational status during operation, with successful/unsuccessful completion of tasks/functions, as well as proper/faulty operational status, being stored in a memory of the host fluid (medication) delivery device 100. Such operational data may be communicated to host remote control device 900 and/or computer 1060 of computer network 1050, and also be stored in a memory of either host remote control device 900 and/or computer 1060 of computer network 1050.

Similar to communication with host remote control device 900, the communication element of host fluid (medication) delivery device 100 may particularly transmit and receive electronic communication from computer 1060 of computer network 1050 using wireless communication standards and protocols (e.g. WiFi, Bluetooth, cellular). As such, it should be understood that the communication element of host fluid (medication) delivery device 100 may particularly be a two-way communication element for allowing the host fluid (medication) delivery device 100 to communicate with computer 1060 of computer network 1050. In such an embodiment, computer 1060 of computer network 1050 also includes a two-way communication element which may also comprise a receiver and a transmitter, such as a transceiver, for allowing the computer 1060 of computer network 1050 to transmit and receive the information sent by the host fluid (medication) delivery device 100. Thus, in addition to being programmed to receive and perform instructions from computer 1060 of computer network 1050 the, the host fluid (medication) delivery device 100 may transmit data (signals) via the transceiver back to computer 1060 of computer network 1050. Thus, host fluid (medication) delivery device 100 and the computer 1060 of computer network 1050 may contain all the computer programs and electronic circuitry needed to allow a clinician to program the desired flow patterns and rates, and adjust the program(s) as necessary. Such circuitry may include one or more microprocessors, digital and analog integrated circuits, resistors, capacitors, transistors and other semiconductors and other electronic components known to those skilled in the art.

Host treatment apparatus 1000 (comprising host fluid (medication) delivery device 100 and optionally host remote control device 900) may particularly report on medication delivery operation of the host fluid (medication) delivery device 100, such a delivery status, to a host treatment application 1100 (computer software program) of computer 1060 of computer network 1050 via an internet connection. The host treatment application 1100 of computer 1060 of computer network 1050, which may be stored in a non-transitory computer-readable storage medium 1090 of the computer 1060, may compile the data as part of a host treatment database 1120 (also stored in a non-transitory memory 1090), and report the status of medication delivery for a plurality of host fluid (medication) delivery devices 100 to the clinician, and alert the clinician as to which host fluid (medication) delivery devices 100 have not indicated medication delivery as being successful/completed.

As set forth above, operational data of host fluid (medication) delivery device 100, particularly concerning medication delivery, may be stored in a memory of host treatment apparatus 1000, which comprises host fluid (medication) delivery device 100 and optionally host remote control device 900. As a result, the host fluid (medication) delivery device 100 and optionally host remote control device 900 have the ability to store operation data in the event neither of the devices 100, 900 is able to communicate and upload data to the host treatment application 1100, including the host treatment database 1120. If suitable communication is not maintained, the stored data may be communicated to the host treatment application 1100 when suitable communication is reestablished.

In order to distinguish the various host fluid (medication) delivery devices 100 and host remote control devices 900 from each other, each device 100, 900 may include a unique identifier. The unique identifier may be a production lot number and a unique device sequence number within each production lot. The sequence number may be an incremental number given to each device as it manufactured. Therefore, each device 100, 900 may be uniquely numbered and identified.

The unique lot and sequence number may be permanently laser inscribed on the external surface of each device 100, 900 and stored within the memory of each device 100, 900. This permanent marking may be either or both human or machine readable. A machine readable identification may be a bar code, 2D data matrix, or similar identification. This unique identification can also be duplicated on the exterior of the device packaging material. In the foregoing manner, the host fluid (medication) delivery device 100, as well as the host remote control device 900, may be uniquely identified and exclusively associated to a particular host in the host treatment application 1100, particularly in the host treatment database 1120. In other words, in being exclusively associated to a particular host, the host fluid (medication) delivery device 100, as well as the host remote control device 900 are operatively associated with only one host, and not any other additional hosts, within the host treatment database 1120.

In addition to the foregoing, a unique identifier for the medication used in the host fluid (medication) delivery device 100 may also be exclusively associated to a particular host in the host treatment application 1100. Prior to the host fluid (medication) delivery device 100 being installed on the host, the host fluid (medication) delivery device 100 may be filled with medication by the clinician, who may record the unique identifier for the medication (e.g. from the packaging) in the host treatment application, 1100, particularly the host treatment database 1120, along with the unique identifiers for the host fluid (medication) delivery device 100 and host remote control device 900, as well as the host's identity.

As such, a host treatment application 1100, and more particularly a host treatment database 1120, may be created to monitor and report the status of drug delivery for each host in real time. Such may comprise unique identifiers being established for each of the host fluid (medication) delivery device 100, host remote control device 900 and the medication. If two or more of the foregoing components are provided as part of a kit, it may also be possible to uniquely identify each of the components with a single unique identifier (e.g. a kit identifier) which can ultimately be broken into discrete identifiers maintained by the manufacturer(s).

Once the unique identifiers for each of the host fluid (medication) delivery device 100, optionally the host remote control device 900 and/or the medication are entered into the host treatment application 1100, and more particularly the host treatment database 1120, a unique host identifier (e.g. social security number, patient number) may be entered into the host treatment application 1100, and more particularly the host treatment database 1120. As a result, the unique identifiers for each of the host fluid (medication) delivery device 100, optionally host remote control device 900 and/or the medication may be exclusively associated with the unique host identifier.

Once the unique host identifier, and the host fluid (medication) delivery device 100, optionally host remote control device 900 and/or the medication unique identifiers are all associated in the host treatment application 1100, and more particularly the host treatment database 1120, the host treatment application 1100 may now display and report on status of devices 100. 900, as well as identify the specific host assigned to each unique device 100, 900.

Thereafter, upon filling the host fluid (medication) delivery device 100 with medication, the host fluid (medication) delivery device 100 and optionally the host remote control device 900 may communicate with the host treatment application 1100 to report that the host fluid (medication) delivery device 100 is now prepared and active. In the process of communication, the unique identifier of the host fluid (medication) delivery device 100 and optionally the host remote control device 900 stored within the memory thereof may be compared with the unique identifier of the host fluid (medication) delivery device 100 and optionally the host remote control device 900 obtained from the bar code packaging to confirm a match thereof. Such may be used as a failsafe confirmation to confirm the scanned unique identifier on the host fluid (medication) delivery device 100 and optionally the host remote control device 900 are associated with the same host.

After activation of the host fluid (medication) delivery device 100 and communication of the unique identifiers for the host fluid (medication) delivery device 100 and optionally the host remote control device 900 to the host treatment application 1100, and more particularly the host treatment database 1120, the fluid (medication) delivery device 100 will continue to operate as pre-programmed or directed by software (e.g. medication delivery manager) stored on the host fluid (medication) delivery device 100 and optionally the host remote control device 900, or the computer 1060 of computer network 1050.

Using one or more sensors and/or signals, the host fluid (medication) delivery device 100 and optionally the host remote control device 900 may report compliance status with pre-programed events/operations to the computer 1060 of computer network 1050, and more particularly the host treatment database 1120 of host treatment application 1100. Such events may include, but are not limited to whether the host fluid (medication) delivery device 100 and optionally the host remote control device 900 are operating properly; whether the cannula(s) (e.g. 176, 376, 377, 476) is inserted properly, particularly by the transcutaneous access tool insertion mechanism (e.g. 180, 280, 380, 480); whether the sensor(s) (e.g. 122a, 122b, 320a, 320b) are inserted properly, particularly by the transcutaneous access tool insertion mechanism (e.g. 180, 280, 380, 480); whether the fluid drive mechanism 150 is operating properly to deliver the medication contained in the medication delivery device to the host; whether medication delivery is complete.

Using one or more sensors and/or signals, the host fluid (medication) delivery device 100 and optionally the host remote control device 900 may report non-compliance status of pre-programmed events/operations to the computer 1060 of computer network 1050, and more particularly the host treatment database 1120 of host treatment application 1100, such as by providing an alert function for start-up errors, drive system errors, occlusions, and other device errors (e.g. microprocessor).

Thus, the host treatment apparatus 1000, and more particularly the host fluid (medication) delivery device 100 and optionally the host remote control device 900, may communicate in real time (or periodically) with the host treatment application 1100. The host treatment application 1100 may monitors, tracks, and report expected or unexpected events of either of the host fluid (medication) delivery device 100 and optionally the host remote control device 900 of the host treatment apparatus 1000.

If the host treatment apparatus 1000, and more particularly the host fluid (medication) delivery device 100 completes its programmed functions as planned, the host treatment apparatus 1000 reports such to the host treatment application 1100. After receiving notification of such from host treatment apparatus 1000, a processor 1080 of the computer 1060 running the host treatment application 1100 may report successful status of such to a client user 1140 of the host treatment application 1100, i.e. that the host received the medication for treatment as expected. If the host treatment apparatus 1000, and more particularly the host fluid (medication) delivery device 100 does not complete its programmed functions as planned, an error/alert is reported to host treatment application 1100 and reported to client users 1140 in the same manner.

The host treatment database 1120 may be accessed and used by a client user 1140, such as the manufacturer(s) of the host treatment apparatus 1000 (comprising host fluid (medication) delivery device 100 and optionally the host remote control device 900), the medication manufacturer, the health care provider (e.g. doctor nurse, clinician), the host/patient, a designee of the host/patient or other previously identified individual or institution having a need to monitor the host treatment database 1120, particularly for non-compliance of medication delivery. The non-compliance (or compliance) notification of proper medication delivery may be accomplished particularly by the manufacturer(s) of the host treatment apparatus 1000 (comprising host fluid (medication) delivery device 100 and optionally the host remote control device 900) or the medication manufacturer hosting a internet accessible, server based computer software application, and/or sending text messages, email, phone calls or other communication methods. The health care provider can follow up on reported non-compliance issues in real time and without host/patient involvement.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

What is claimed is:

1. A method of treating a host with a medication, the method comprising:
    assigning a unique host treatment apparatus identifier to a host treatment apparatus comprising a host medication delivery device which delivers medication into tissue of the host subcutaneously, wherein the unique host treatment apparatus identifier distinguishes the host treatment apparatus from a plurality of other host treatment apparatuses, and wherein the host medication delivery device includes a sensor, wherein the sensor is used to measure a physiological parameter associated with the tissue and disposed within the host medication delivery device;
    assigning a unique host identifier to the host to be treated by the host treatment apparatus, wherein the unique host identifier distinguishes the host from a plurality of other hosts;
    storing the unique host identifier and the unique host treatment apparatus identifier on at least one remote server of a network, and associating the unique host identifier and the unique host treatment apparatus identifier on the at least one remote server of the network such that the unique host treatment apparatus identifier is exclusively associated with the unique host identifier to the exclusion of the other hosts;
    filling the host medication delivery device with medication;
    activating the host treatment apparatus;
    coupling the host medication delivery device to the host such that the host medication delivery device is arranged to deliver the medication contained in the host medication delivery device to the host subcutaneously;
    introducing the host medication delivery device including the sensor into the tissue;
    operating the host medication delivery device to deliver the medication contained in the host medication delivery device into the tissue of the host subcutaneously; and
    confirming delivery of the medication from the host medication delivery device to the host, wherein confirming delivery of the medication comprises using the sensor to measure the physiological parameter within a predetermined time period after delivery of the medication;
    operating the host treatment apparatus such that the host treatment apparatus communicates wirelessly to the at least one remote server of the network to report confirmation of the delivery of the medication from the host medication delivery device to the host to the at least one remote server of the network;
    wherein the at least one remote server of the network receives a wireless communication from the host treatment apparatus as to the delivery of the medication from the host medication delivery device to the host while the host medication delivery device is coupled to the host; and
    in response to the wireless communication from the host treatment apparatus as to the delivery of the medication from the host medication delivery device to the host, the at least one remote server of the network reports the delivery of the medication from the host medication delivery device to the host to at least one client user of the network while the host medication delivery device is coupled to the host.

2. The method of claim 1 wherein:
the step(s) of storing the unique host identifier and the unique host treatment apparatus identifier on at least one remote server of a network, and associating the unique host identifier and the unique host treatment apparatus identifier on the at least one remote server of the network such that the unique host treatment apparatus identifier is exclusively associated with the unique host identifier further comprises
    associating the unique host identifier and the unique host treatment apparatus identifier in a computer software program which resides on the at least one remote server of the network; and
the step of operating the host treatment apparatus such that the host treatment apparatus communicates wirelessly to the at least one remote server of the network a delivery of the medication from the host medication delivery device to the host further comprises
    operating the host treatment apparatus such that the host treatment apparatus communicates wirelessly to the computer software program residing on the at least one remote server of the network a delivery of the medication from the host medication delivery device to the host.

3. The method of claim 1 wherein:
the unique host treatment apparatus identifier is a unique identifier of the host medication delivery device.

4. The method of claim 1 wherein:
the host treatment apparatus further comprises a host remote control device, wherein the host medication delivery device and the host remote control device are configured to communicate wirelessly to each other.

5. The method of claim 1 further comprising:
introducing the host medication delivery device including the sensor into the tissue such that the tissue is in contact with the sensor; and
forming a depot in the tissue with the medication, wherein the depot reduces the tissue contact with the sensor by displacing the tissue from the sensor.

6. The method of claim 5 wherein:
the predetermined time period is less than a time required for the depot to be completely absorbed into the tissue and the tissue reestablishes contact with the sensor where the depot was located.

7. The method of claim 1 wherein:
confirming delivery of the medication from the host medication delivery device to the host further comprises
    determining a value of the physiological parameter measured within the predetermined time period after delivery of the medication;
    providing a predetermined representative value for the physiological parameter, wherein the predetermined representative value of the physiological parameter is stored with at least one of the host treatment apparatus and the at least one remote server of the network; and
    determining that the measured value of the physiological parameter within the predetermined time period after delivery of the medication is less than or greater than the predetermined representative value for the physiological parameter stored with at least one of the host treatment apparatus and the at least one remote server of the network.

8. The method of claim 1 further comprising:
after introducing the host medication delivery device including the sensor into the tissue, using the sensor to measure the physiological parameter before delivering the medication into the tissue; and
wherein confirming delivery of the medication from the host medication delivery device to the host further comprises
determining a value of the physiological parameter measured before delivering the medication;
determining a value of the physiological parameter measured within the predetermined time period after delivery of the medication; and
determining that the value of the physiological parameter measured within the predetermined time after delivery of the medication is less than or greater than the value of the physiological parameter measured before delivering the medication into the tissue.

9. The method of claim 1 further comprising:
after introducing the host medication delivery device including the sensor into the tissue, using the sensor to measure the physiological parameter before delivering the medication into the tissue; and
wherein confirming delivery of the medication from the host medication delivery device to the host further comprises
determining a value of the physiological parameter measured before delivering the medication;
determining a value of the physiological parameter measured within the predetermined time period after delivery of the medication;
determining a numerical difference between the value of the physiological parameter measured before delivering the medication into the tissue, and the value of the physiological parameter measured within the predetermined time after delivering the medication into the tissue;
providing a predetermined representative value for the numerical difference of the physiological parameter, wherein the predetermined representative value for the numerical difference of the physiological parameter is stored with at least one of the host treatment apparatus and the at least one remote server of the network; and
determining the numerical difference between the two measured values of the physiological parameter is greater than the predetermined representative value for the numerical difference of the physiological parameter stored with at least one of the host treatment apparatus and the at least one remote server of the network.

10. The method of claim 1 further comprising:
after introducing the host medication delivery device including the sensor into the tissue, using the sensor to measure the physiological parameter before delivering the medication into the tissue; and
wherein confirming delivery of the medication from the host medication delivery device to the host further comprises
determining a value of the physiological parameter measured before delivering the medication;
determining a value of the physiological parameter measured within the predetermined time period after delivery of the medication;
determining a percentage change between the value of the physiological parameter measured before delivering the medication into the tissue, and the value of the physiological parameter measured within the predetermined time after delivering the medication into the tissue;
providing a predetermined representative value for the percentage change of the physiological parameter, wherein the predetermined representative value for the percentage change of the physiological parameter is stored with at least one of the host treatment apparatus and the at least one remote server of the network; and
determining the percentage change between the two measured values of the physiological parameter is greater than the predetermined representative value for the percentage change of the physiological parameter stored with at least one of the host treatment apparatus and the at least one remote server of the network.

11. The method of claim 1 wherein:
wherein introducing the host medication delivery device including the sensor into the tissue further comprises
introducing the host medication delivery device including the sensor into the tissue such that the tissue is in contact with the sensor;
forming a depot in the tissue with the medication, wherein the sensor is at least partially within the depot and the depot reduces the tissue contact with the sensor by displacing the tissue from the sensor; and
wherein confirming delivery of the medication from the host medication delivery device to the host, wherein confirming delivery of the medication comprises using the sensor to measure the physiological parameter within a predetermined time period after delivery of the medication further comprises
confirming delivery of the medication from the host medication delivery device to the host, wherein confirming delivery of the medication comprises using the sensor to measure the physiological parameter within a predetermined time period after delivery of the medication while the sensor is within the depot.

12. The method of claim 11 wherein:
confirming delivery of the medication from the host medication delivery device to the host further comprises
determining a value of the physiological parameter while the sensor is within the depot;
providing a predetermined representative value for the physiological parameter, wherein the predetermined representative value of the physiological parameter is stored with at least one of the host treatment apparatus and the at least one remote server of the network; and
determining that the measured value of the physiological parameter while the sensor is within the depot is less than or greater than the predetermined representative value for the physiological parameter stored with at least one of the host treatment apparatus and the at least one remote server of the network.

13. The method of claim 11 further comprising:
after introducing the host medication delivery device including the sensor into the tissue, using the sensor to measure the physiological parameter before delivering the medication into the tissue; and wherein confirming delivery of the medication from the host medication delivery device to the host further comprises determining a value of the physiological parameter measured before delivering the medication;

determining a value of the physiological parameter measured while the sensor is within the depot; and determining that the value of the physiological parameter measured while the sensor is within the depot is less than or greater than the value of the physiological parameter measured before delivering the medication into the tissue.

14. The method of claim 11 further comprising:

after introducing the host medication delivery device including the sensor into the tissue, using the sensor to measure the physiological parameter before delivering the medication into the tissue; and wherein confirming delivery of the medication from the host medication delivery device to the host further comprises determining a value of the physiological parameter measured before delivering the medication;

determining a value of the physiological parameter measured while the sensor is within the depot;

determining a numerical difference between the value of the physiological parameter measured before delivering the medication into the tissue, and the value of the physiological parameter measured while the sensor is within the depot;

providing a predetermined representative value for the numerical difference of the physiological parameter, wherein the predetermined representative value for the numerical difference of the physiological parameter is stored with at least one of the host treatment apparatus and the at least one remote server of the network; and determining the numerical difference between the two measured values of the physiological parameter is greater than a predetermined representative value for the numerical difference of the physiological parameter stored with at least one of the host treatment apparatus and the at least one remote server of the network.

15. The method of claim 11 further comprising:

after introducing the host medication delivery device including the sensor into the tissue, using the sensor to measure the physiological parameter before delivering the medication into the tissue; and wherein confirming delivery of the medication from the host medication delivery device to the host further comprises determining a value of the physiological parameter measured before delivering the medication;

determining a value of the physiological parameter measured while the sensor is within the depot;

determining a percentage change between the value of the physiological parameter measured before delivering the medication into the tissue, and the value of the physiological parameter measured while the sensor is within the depot;

providing a predetermined representative value for the percentage change of the physiological parameter, wherein the predetermined representative value for the percentage change of the physiological parameter is stored with at least one of the host treatment apparatus and the at least one remote server of the network; and determining the percentage change between the two measured values of the physiological parameter is greater than a predetermined representative value for the percentage change of the physiological parameter stored with at least one of the host treatment apparatus and the at least one remote server of the network.

\* \* \* \* \*